US009345446B2

(12) United States Patent
Sato

(10) Patent No.: US 9,345,446 B2
(45) Date of Patent: May 24, 2016

(54) ULTRASONIC DIAGNOSIS APPARATUS, IMAGE PROCESSING APPARATUS, AND IMAGE PROCESSING METHOD

(71) Applicant: Takeshi Sato, Nasushiobara (JP)

(72) Inventor: Takeshi Sato, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 340 days.

(21) Appl. No.: 13/688,556

(22) Filed: Nov. 29, 2012

(65) Prior Publication Data
US 2013/0150717 A1 Jun. 13, 2013

(30) Foreign Application Priority Data
Dec. 8, 2011 (JP) ................................. 2011-268884

(51) Int. Cl.
*A61B 8/06* (2006.01)
*A61B 8/14* (2006.01)
(Continued)

(52) U.S. Cl.
CPC ..... *A61B 8/06* (2013.01); *A61B 8/14* (2013.01); *A61B 8/463* (2013.01); *A61B 8/466* (2013.01); *A61B 8/483* (2013.01); *A61B 8/488* (2013.01); *A61B 8/5207* (2013.01); *A61B 8/5223* (2013.01)

(58) Field of Classification Search
CPC .......... A61B 8/06; A61B 8/14; A61B 8/5207; A61B 8/5223; A61B 8/463; A61B 8/466
See application file for complete search history.

(56) References Cited

U.S. PATENT DOCUMENTS 4,993,417 A 2/1991 Seo
5,669,387 A * 9/1997 Mine .............................. 600/455
(Continued)

FOREIGN PATENT DOCUMENTS

CN 101352354 A 1/2009
CN 101563626 A 10/2009
(Continued)

OTHER PUBLICATIONS

Office Action and Search Report issued on May 30, 2014 in the corresponding Chinese Patent Application No. 201210518548.6 (with English Translation of Category of Cited Documents).
(Continued)

*Primary Examiner* — Bo J Peng
(74) *Attorney, Agent, or Firm* — Oblon, McClelland, Maier & Neustadt, L.L.P.

(57) ABSTRACT

An ultrasonic diagnosis apparatus according to an embodiment includes a processor, an image generator, a detector, and a controller. The processor is configured to acquire two-dimensional or three-dimensional blood flow information in time sequence in a scan range formed of a plurality of scan lines, from two-dimensional or three-dimensional echo data collected through ultrasound transmission/reception performed in the scan range. The image processor is configured to generate blood flow images in time sequence from the two-dimensional or three-dimensional blood flow information in time sequence in the scan range. The detector is configured to detect movement information in time sequence of speckles in a preset two-dimensional or three-dimensional region of interest, among the blood flow images in time sequence. The controller is configured to control a predetermined display to display movement information data that is data based on the movement information in time sequence.

12 Claims, 17 Drawing Sheets

(51) Int. Cl.
*A61B 8/08* (2006.01)
*A61B 8/00* (2006.01)

(56) References Cited

U.S. PATENT DOCUMENTS

| | | | |
|---|---|---|---|
| 6,048,312 A * | 4/2000 | Ishrak et al. | 600/443 |
| 6,618,493 B1 * | 9/2003 | Torp et al. | 382/131 |
| 8,208,703 B2 | 6/2012 | Kawagishi et al. | |
| 8,241,218 B2 | 8/2012 | Hirama | |
| 2004/0006266 A1 * | 1/2004 | Ustuner et al. | 600/407 |
| 2005/0080329 A1 * | 4/2005 | Uchibori | 600/407 |
| 2005/0222506 A1 * | 10/2005 | Takimoto et al. | 600/455 |
| 2010/0004540 A1 | 1/2010 | Thiele | |
| 2011/0092819 A1 | 4/2011 | Takimoto et al. | |
| 2011/0301470 A1 | 12/2011 | Sato et al. | |

FOREIGN PATENT DOCUMENTS

| | | |
|---|---|---|
| CN | 101732036 A | 6/2010 |
| CN | 102038522 A | 5/2011 |
| JP | S53-057867 A | 5/1978 |
| JP | 64-43237 | 2/1989 |
| JP | H11-164831 A | 6/1999 |
| JP | 2000-342585 A | 12/2000 |
| JP | 3724846 | 9/2005 |
| JP | 2009-28366 A | 2/2009 |
| JP | 2010-508881 A | 3/2010 |
| JP | 2010-110612 A | 5/2010 |
| JP | 4660126 | 1/2011 |
| JP | 2011-87710 A | 5/2011 |

OTHER PUBLICATIONS

Office Action issued Sep. 29, 2015, in Japanese Patent Application No. 2011-268884.

Office Action mailed Mar. 29, 2016 in Japanese Patent Application No. 2011-268884.

* cited by examiner

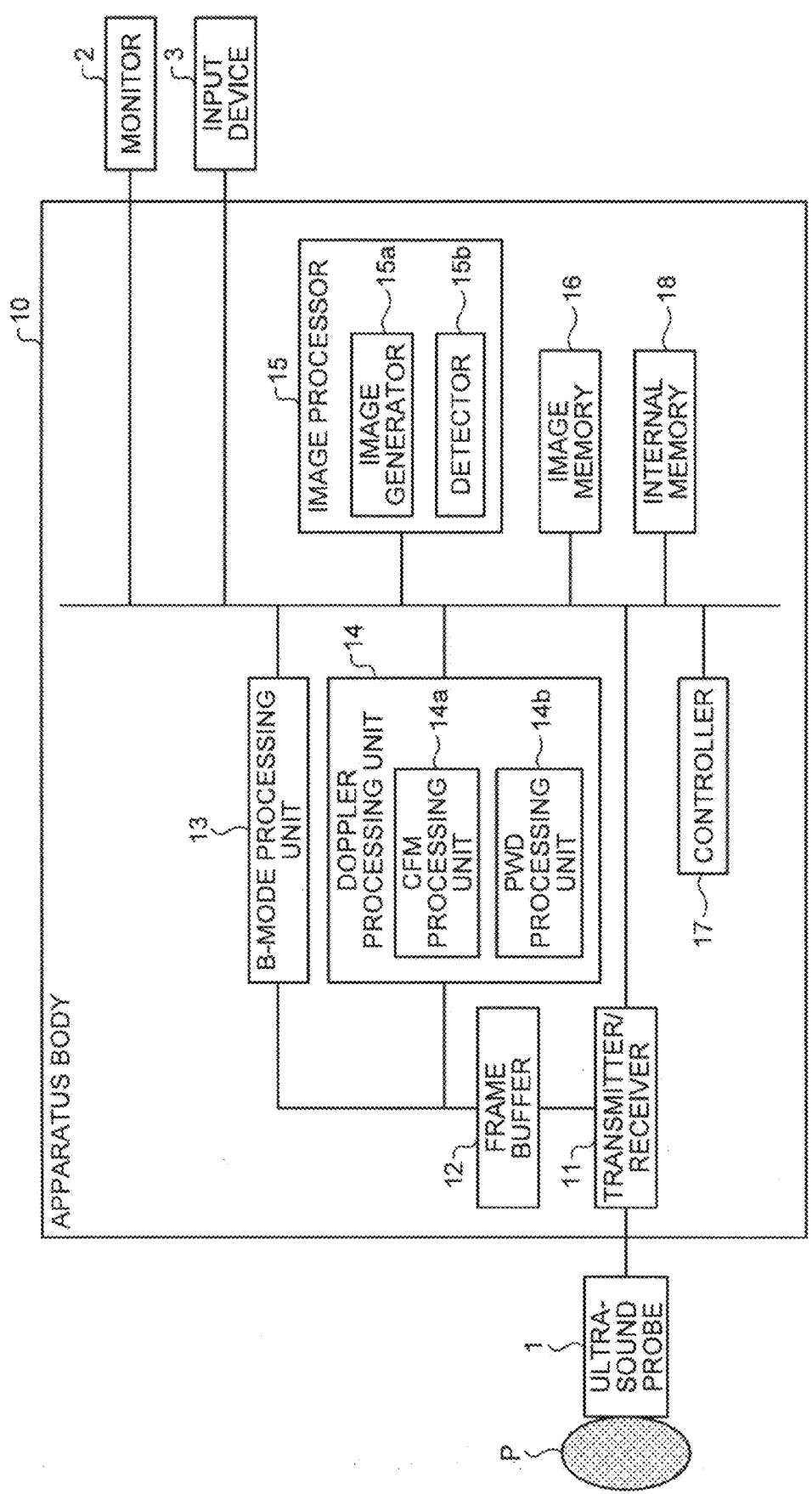

FIG.10
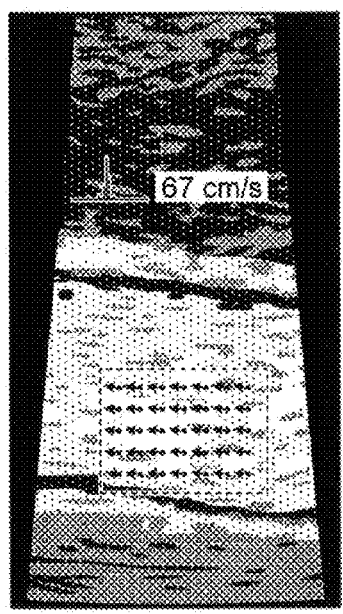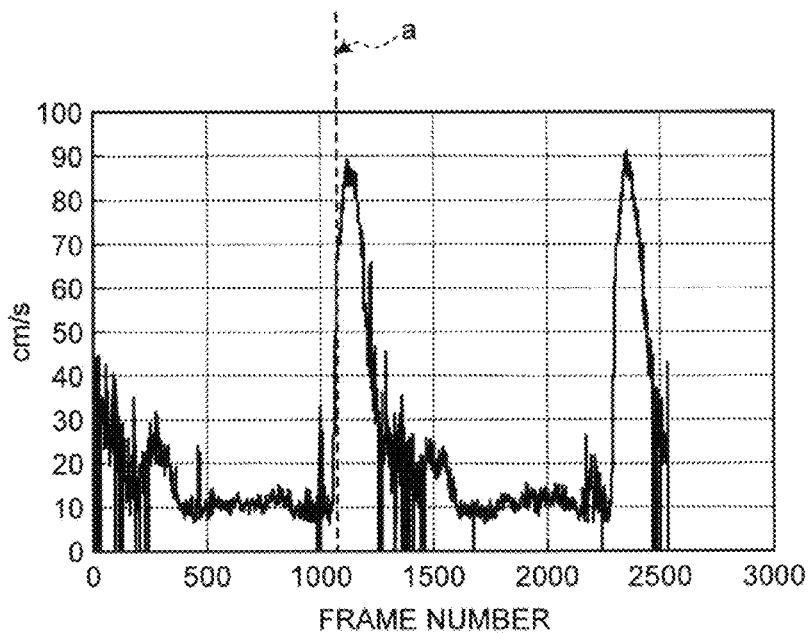

FIG.17
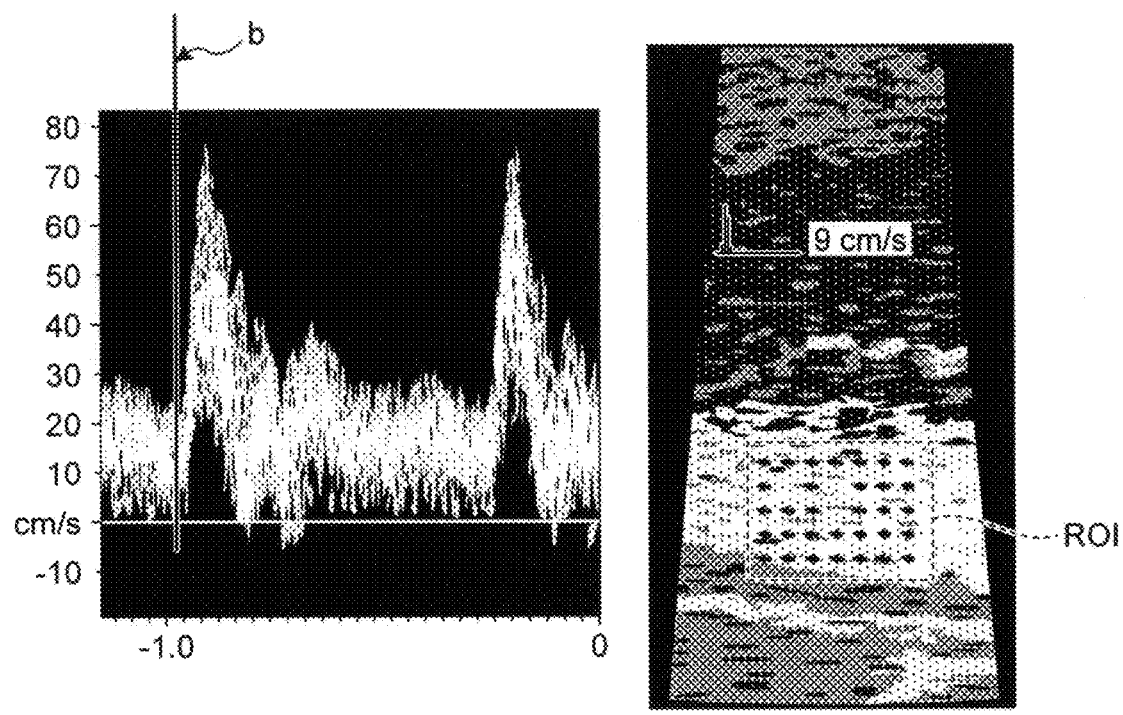
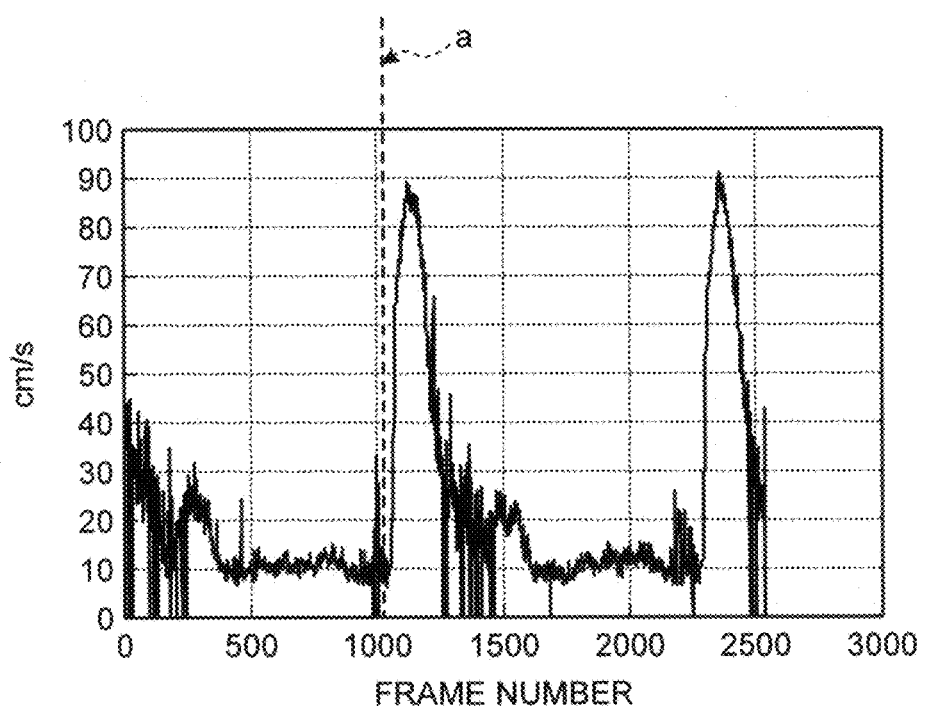

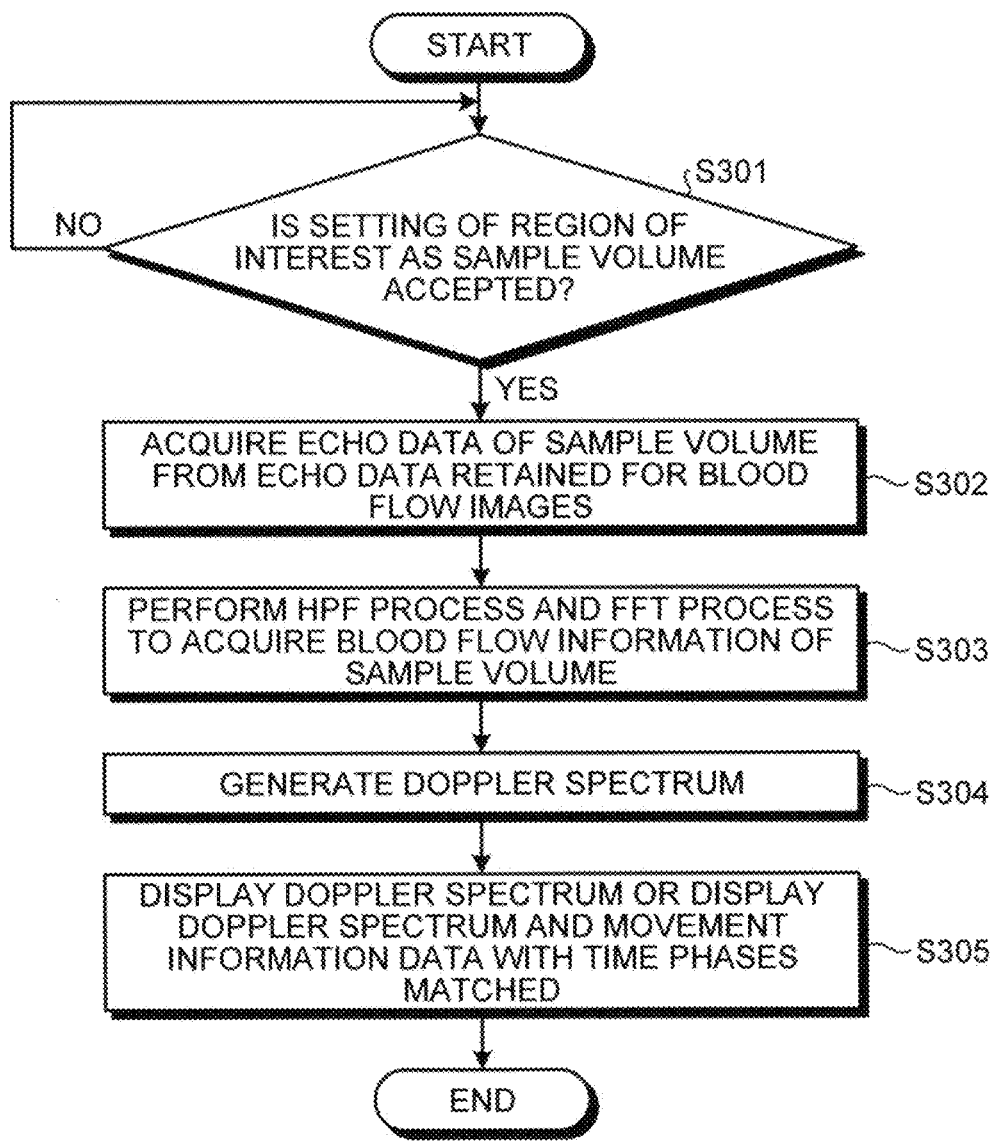

ULTRASONIC DIAGNOSIS APPARATUS, IMAGE PROCESSING APPARATUS, AND IMAGE PROCESSING METHOD

CROSS-REFERENCE TO RELATED APPLICATIONS

This application is based upon and claims the benefit of priority from Japanese Patent Application No. 2011-268884, filed on Dec. 8, 2011, the entire contents of all of which are incorporated herein by reference.

FIELD

Embodiments described herein relate generally to an ultrasonic diagnosis apparatus, an image processing apparatus, and an image processing method.

BACKGROUND

Ultrasonic diagnosis apparatuses have been widely used for observation and diagnosis of blood flows in living bodies. An ultrasonic diagnosis apparatus generates and displays blood flow information from reflected waves of ultrasound by a Doppler method based on the Doppler effect. The blood flow information generated and displayed by the ultrasonic diagnosis apparatus includes a color Doppler image, a Doppler spectrum, etc.

A color Doppler image is an ultrasonic image captured by a Color Flow Mapping (CFM) method. In the CFM method, transmission/reception of ultrasound is performed on a plurality of scan lines in a region (two-dimensional region or three-dimensional region) including a site to be observed or diagnosed. In the CFM method, a moving target indicator (MTI) filter is used to remove frequency components derived from the motion of tissues from echo data and extract data of blood flow components, and the data of blood flow components is subjected to frequency analysis by autocorrelation, whereby the velocity of blood flow, the distribution of blood flow, and the power of blood flow are calculated. The color Doppler image is an ultrasonic image that two-dimensionally displays the distribution of those calculation results in color. In the CFM method, a method called alternate scan for improving the ability of detecting blood flows at low flow rates and a method that allows capture of color Doppler images at high frame rates are known.

On the other hand, a Doppler spectrum is data collected by a Continuous Wave (CW) Doppler method or a Pulsed Wave (PW) Doppler method. In the CWD method or the PWD method, transmission/reception of ultrasound is performed in time sequence on a single scan line including a site to be observed or diagnosed. In the CWD method, a high pass filter (HPF) having similar filter characteristics as the MTI filter is used to extract data of blood flow components on the scan line from time-sequential echo data. In the PWD method, data of blood flow components in a sample volume (for example, one point) on a scan line is extracted from the time-sequential echo data in the sample volume (also called a range gate) set on the single scan line.

In the CWD method and the PWD method, the blood flow information (the velocity of blood flow, the distribution of blood flow, and the power of blood flow) is calculated by performing frequency analysis on such data of blood flow components by a fast fourier transform (FFT) method. In the CWD method, the average blood flow information on a scan line is output, whereas in the PW Doppler method, the blood flow information in a sample volume on a scan line is output.

The Doppler spectrum is an image of a spectrum obtained by plotting information of the calculation results in time sequence. The display of a Doppler spectrum is also called FFT display.

In the FFT display with a single scan line, the blood flow behavior in a one-dimensional region of interest can be observed precisely with good time resolution. However, the blood flow behavior in a two-dimensional or three-dimensional region of interest cannot be observed with the FFT display.

BRIEF DESCRIPTION OF THE DRAWINGS

FIG. 1 is a diagram for explaining an exemplary configuration of an ultrasonic diagnosis apparatus according to a first embodiment;

FIG. 7A, FIG. 7B, FIG. 8A, FIG. 8B, FIG. 9, and FIG. 10 are diagrams for explaining specific examples of movement information data displayed by a controller according to the first embodiment;

FIG. 14, FIG. 15, FIG. 16, and FIG. 17 are diagrams for explaining an example of a process procedure executed by an image processor according to a second embodiment;

FIG. 21 is a flowchart for explaining processing in an ultrasonic diagnosis apparatus according to the third embodiment.

DETAILED DESCRIPTION

Figure 2A:
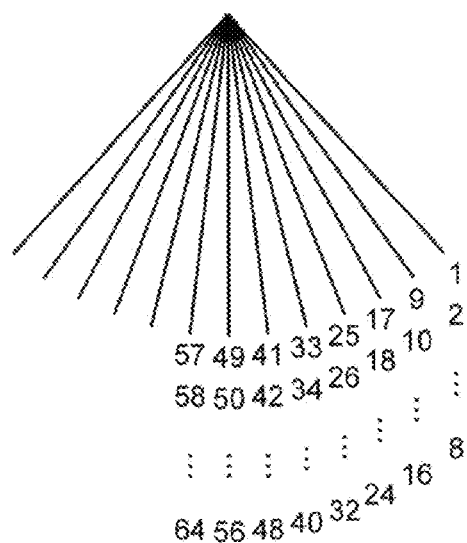
FIG. 2A, FIG. 2B, and FIG. 2C are diagrams for explaining manners of scanning in a variety of color flow mapping methods executed by the ultrasonic diagnosis apparatus according to the first embodiment.

An ultrasonic diagnosis apparatus according to an embodiment includes a processor, an image generator, a detector, and a controller. The processor is configured to acquire two-dimensional or three-dimensional blood flow information in time sequence in a scan range formed of a plurality of scan lines, from two-dimensional or three-dimensional echo data collected through ultrasound transmission/reception performed in the scan range. The image processor is configured to generate blood flow images in time sequence from the two-dimensional or three-dimensional blood flow information in time sequence in the scan range. The detector is configured to detect movement information in time sequence of speckles in a preset two-dimensional or three-dimensional region of interest, among the blood flow images in time sequence. The controller is configured to control a predetermined display to display movement information data that is data based on the movement information in time sequence.

Embodiments of an ultrasonic diagnosis apparatus will be described in detail below with reference to the accompanying drawings.

First of all, an exemplary configuration of an ultrasonic diagnosis apparatus according to a first embodiment will be described. FIG. 1 is a diagram for explaining an exemplary configuration of an ultrasonic diagnosis apparatus according to the first embodiment. As illustrated in FIG. 1, the ultrasonic diagnosis apparatus according to the first embodiment has an ultrasound probe 1, a monitor 2, an input device 3, and an apparatus body 10.

The ultrasound probe 1 has a plurality of piezoelectric vibrators, which generate an ultrasonic wave based on a drive signal supplied from a transmitter/receiver 11 of the apparatus body 10 as described later. The ultrasound probe 1 receives a reflected wave from a subject P and converts the received reflected wave into an electrical signal. The ultrasound probe 1 mainly has a matching layer and an acoustic lens provided on the piezoelectric vibrators, and a backing material for preventing propagation of ultrasound backward from the piezoelectric vibrators. The ultrasound probe 1 is removably connected to the apparatus body 10.

When an ultrasonic wave is transmitted from the ultrasound probe 1 to a subject P, the transmitted ultrasonic wave is successively reflected on a surface of discontinuity of acoustic impedance in tissues inside the body of the subject P and is received as an echo signal by the piezoelectric vibrators of the ultrasound probe 1. The amplitude of the received echo signal depends on the difference in acoustic impedance on the surface of discontinuity on which the ultrasonic wave is reflected. In a case where the transmitted ultrasonic pulse is reflected on a moving blood flow or surface such as a heart wall, the echo signal undergoes a frequency shift (Doppler shift) depending on the velocity component of the moving target relative to the ultrasound transmission direction due to the Doppler effect.

It is noted that the first embodiment is applicable to a case where the subject P is two-dimensionally scanned with the ultrasound probe 1 that is a one-dimensional ultrasound probe having a plurality of piezoelectric vibrators arranged in a row, and to a case where the subject P is three-dimensionally scanned with the ultrasound probe 1 in which a plurality of piezoelectric vibrators of a one-dimensional ultrasound probe are mechanically swung, or with the ultrasound probe 1 that is a two-dimensional ultrasound probe in which a plurality of piezoelectric vibrators are arranged in a two-dimensional array. Here, the one-dimensional ultrasound probe can also one-dimensionally scan the subject P on one scan line. The two-dimensional ultrasound probe can also two-dimensionally scan the subject P by transmitting the focused ultrasound.

The ultrasonic diagnosis apparatus according to the first embodiment can capture a color Doppler image as described later. The ultrasonic diagnosis apparatus according to the first embodiment can also collect a Doppler spectrum in a sample volume set in a B-mode image, a color Doppler image, or an image having a color Doppler image superimposed on part of a B-mode image, as described later. Therefore, depending on the type of the image to be collected, the ultrasound probe 1 may be changed, for example, from an ultrasound probe 1 for performing the Color Flow Mapping (CFM) method to an ultrasound probe 1 for performing the Continuous Wave (CW) Doppler method or the Pulsed Wave (PW) Doppler method. The sample volume above may also be called a range gate.

The input device 3 has, for example, a mouse, a keyboard, a button, a panel switch, a touch command screen, a foot switch, and a trackball for accepting a variety of setting requests from the operator of the ultrasonic diagnosis apparatus and transferring the accepted setting requests to the apparatus body 10.

For example, the input device 3 accepts from the operator the setting of a Region Of Interest (ROI) for an image processor 15 described later to perform image processing. In the first embodiment, the region of interest accepted by the input device 3 will be detailed later.

The monitor 2 displays Graphical User Interfaces (GUI) for the operator of the ultrasonic diagnosis apparatus to input a variety of setting requests using the input device 3 or displays an ultrasonic image generated in the apparatus body 10.

The apparatus body 10 is an apparatus for generating an ultrasonic image based on the reflected wave received by the ultrasound probe 1. The apparatus body 10 has a transmitter/receiver 11, a frame buffer 12, a B-mode processing unit 13, a Doppler processing unit 14, an image processor 15, an image memory 16, a controller 17, and an internal memory 18, as illustrated in FIG. 1.

The transmitter/receiver 11 has a trigger generating circuit, a transmission delay circuit, a pulsar circuit, and the like for supplying a drive signal to the ultrasound probe 1. The pulsar circuit repeatedly generates a rate pulse for forming transmission ultrasound at a predetermined Pulse Repetition Frequency (PRF). The PRF is also called a rate frequency. The transmission delay circuit provides each rate pulse generated by the pulsar circuit with a transmission delay time for each piezoelectric vibrator that is required to focus ultrasonic waves generated from the ultrasound probe 1 into a beam and determine transmission directivity. The trigger generating circuit applies a drive signal (driving pulse) to the ultrasound probe 1 at a timing based on the rate pulse. In other words, the transmission delay circuit adjusts the transmission direction from the piezoelectric vibrator surface as desired by changing the transmission delay time provided to each rate pulse.

The transmitter/receiver 11 has a function capable of instantaneously changing a transmission frequency, a transmission driving voltage, and the like for executing a predetermined scan sequence based on an instruction of the controller 17 described later. In particular, the transmission driving voltage can be changed by a linear amplifier-type transmission circuit capable of instantaneously switching its values or by a mechanism for electrically switching power supply units.

In addition, the transmitter/receiver 11 has an amplifier circuit, an analog/digital (A/D) converter, a reception delay circuit, an adder, a quadrature detection circuit, and the like for performing a variety of processing on the echo signal received by the ultrasound probe 1 to generate echo data. The amplifier circuit performs a gain correction process by amplifying the echo signal for each channel. The A/D converter A/D converts the echo signal having the gain corrected. The reception delay circuit provides digital data with a reception delay time required to determine the reception directivity. The adder performs an addition process for the echo signal processed by the reception delay circuit. The addition process by the adder enhances the echo component from the direction corresponding to the reception directivity of the echo signal. Then, the quadrature detection circuit converts the output signal from the adder into an In-phase signal (I signal) and a Quadrature-phase signal (Q signal) in a baseband range. Then, the quadrature detection circuit stores the I signal and the Q signal (hereinafter referred to as an I/Q signal) as echo data into the frame buffer 12 at the following stage. In this manner, the transmitter/receiver 11 controls the transmission directivity and the reception directivity in transmission/reception of ultrasound.

The frame buffer 12 is a buffer for temporarily storing echo data (I/Q signal) generated by the transmitter/receiver 11. Specifically, the frame buffer 12 retains the I/Q signal in data volume in accordance with its storage capacity. For example, the frame buffer 12 is an first-in/first-out (FIFO) memory, which stores the I/Q signal of predetermined frames, and when the transmitter/receiver 11 newly generates the I/Q signal of one frame, discards the I/Q signal of one frame with the most earliest generation time and stores the newly generated I/Q signal of one frame.

The I/Q signal of one frame is, for example, echo data for generating one ultrasonic image. The transmitter/receiver 11 generates the I/Q signal of one frame by controlling the ultrasound probe 1 to perform ultrasound transmission/reception in a scan range formed of a plurality of scan lines.

The B-mode processing unit 13 reads out the echo data (I/Q signal) generated by the transmitter/receiver 11 from the frame buffer 12 and performs logarithmic amplification, envelope detection processing, logarithmic compression, and the like to generate data (B-mode data) in which the signal intensity is represented by brightness.

The Doppler processing unit 14 reads out the echo data (I/Q signal) generated by the transmitter/receiver 11 from the frame buffer 12 and performs frequency analysis on the read echo data to extract a Doppler shift (Doppler shift frequency), extract blood flow, tissue, or contrast medium echo components due to the Doppler effect using the Doppler shift, and generate data (Doppler data) in which moving target information such as average speed, distribution, and power is extracted at multiple points or one point.

Specifically, as illustrated in FIG. 1, the Doppler processing unit 14 has a CFM processing unit 14a and a PWD processing unit 14b. The CFM processing unit 14a is a processing unit for generating Doppler data for generating a color Doppler image by the CFM method. The CFM processing unit 14a obtains the moving target information of blood flow (blood flow information) in a scan range by autocorrelation.

The PWD processing unit 14b is a processing unit for generating Doppler data for generating a Doppler spectrum by the PWD method. The PWD processing unit 14b acquires the moving target information of blood flow (blood flow information) in a sample volume by performing frequency analysis. For example, the PWD processing unit 14b acquires the moving target information of blood flow (blood flow information) in a sample volume by performing frequency analysis by fast fourier transform (FFT). The PWD processing unit 14b can function as a processing unit that generates Doppler data for generating a Doppler spectrum by the CWD method. The frequency analysis performed by the PWD processing unit 14b may be any method other than fast fourier transform as long as Doppler data from which a Doppler spectrum can be generated can be acquired.

The processing performed by the CFM processing unit 14a and the processing performed by the PWD processing unit 14b will be detailed later. The Doppler processing unit 14 may have a processing unit for performing a tissue Doppler method.

The image processor 15 is a processor that generates image data for display using the data generated by the B-mode processing unit 13 and the Doppler processing unit 14 and performs image processing on the generated image data. The image processor 15 illustrated in FIG. 1 has an image generator 15a and a detector 15b.

The image generator 15a generates an ultrasonic image from the data generated by the B-mode processing unit 13 and the CFM processing unit 14a. More specifically, the image generator 15a generates a B-mode image that represents the power of a reflected wave with brightness from the B-mode data generated by the B-mode processing unit 13. The image generator 15a also generates a color Doppler image as a velocity image, a distribution image, a power image, or an image including a combination thereof that represents moving target information (blood flow information) from the Doppler data generated by the CFM processing unit 14a. For example, the image generator 15a generates a power image in which the color tone is varied in red in accordance with values of power. In addition to the color Doppler image for color display, the image generator 15a can generate, for example, a power image in grayscale in which the brightness is varied in grayscale in accordance with values of power.

An image such as a color Doppler image generated by the image generator 15a from the data generated by the CFM processing unit 14a is hereinafter referred to as a "blood flow image."

The image generator 15a further generates a Doppler spectrum in which the velocity information of blood flow is plotted in time sequence, from the Doppler data generated by the PWD processing unit 14b. Specifically, the image generator 15a generates a temporal change curve in which the vertical axis represents the velocity of blood flow in a sample volume and the horizontal axis represents the time. Then, the image generator 15a generates a Doppler spectrum by setting the width in the vertical axis direction in accordance with the variance of blood flow in the sample volume and setting the brightness values in accordance with the power values of blood flow in the sample volume.

Here, the image generator 15a generally scan-converts a scan line signal train in ultrasound scanning into a scan line signal train in a video format typically of television and generates an ultrasonic image (B-mode image or blood flow image) as a display image. Specifically, the image generator 15a generates an ultrasonic image as a display image by performing coordinate transformation in accordance with a manner of scanning of ultrasound with the ultrasound probe 1. The image generator 15a performs various image processing other than scan-convert, for example, image processing (smoothing) of regenerating an image of mean values of brightness using a plurality of image frames after scan-convert, or image processing (edge enhancement) using a differential filter in an image.

When ultrasound transmission/reception is two-dimensionally performed, the image generator 15a generates a two-dimensional B-mode image or a two-dimensional blood flow image as a display image by performing coordinate transformation. When ultrasound transmission/reception is three-dimensionally performed, the image generator 15a generates volume data (three-dimensional B-mode image or three-dimensional blood flow image) and generates a two-dimensional image to be displayed on the monitor 2 from the volume data through a variety of rendering processing.

The image generator 15a also generates a composite image in which character information such as various parameters, a scale, a body mark, etc. is combined with a variety of images. The image generator 15a also generates a superimposed image in which a variety of images is superimposed, such as a superimposed image including a B-mode image and a color Doppler image, or generates images for concurrently displaying a variety of images.

The detector 15b illustrated in FIG. 1 is a processing unit for performing image processing on the image data generated by the image generator 15a. Specifically, the detector 15b performs speckle tracking in which speckles in an image are tracked. The processing performed by the detector 15b in the first embodiment will be detailed later.

The image memory 16 is a memory for storing a variety of data generated by the image generator 15a. The image memory 16 can also store the data (raw data) generated by the B-mode processing unit 13 and the Doppler processing unit 14. The image memory 16 can also store data retained by the frame buffer 12, as necessary.

The internal memory 18 stores a control program for performing ultrasound transmission/reception, image processing, and display processing, diagnosis information (for example, a patient ID, the doctor's observation, etc.), and various data such as diagnosis protocol and a variety of body marks. The internal memory 18 is also used to store data stored by the image memory 16, as necessary. The data stored by the internal memory 18 may be transferred to an external peripheral device via a not-shown interface.

The controller 17 controls the entire processing in the ultrasonic diagnosis apparatus. Specifically, the controller 17 controls the processing in the transmitter/receiver 11, the B-mode processing unit 13, the Doppler processing unit 14, and the image processor 15, based on a variety of setting requests input through the input device 3 by the operator and a variety of control programs and data read from the internal memory 18. The controller 17 also controls such that the data stored by the image memory 16 and the GUIs for the operator to designate a variety of processing are displayed on the monitor 2. The display of a Doppler spectrum by the PWD method or the CWD method is also called "FFT display." The display of a blood flow image (color Doppler image) by the CFM method is hereinafter referred to as color Doppler display.

Figure 2B:
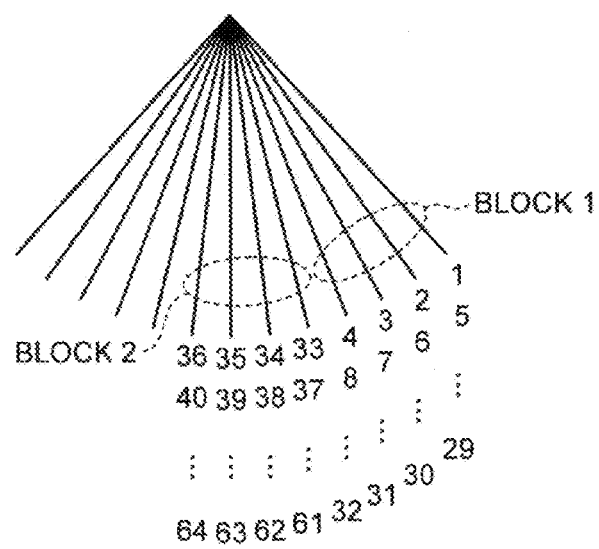
Figure 2C:
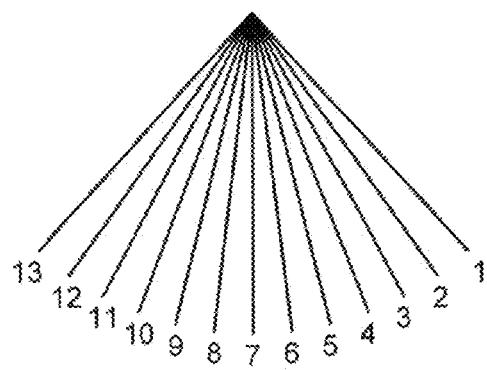

The overall configuration of the ultrasonic diagnosis apparatus according to the first embodiment has been described above. With such a configuration, the ultrasonic diagnosis apparatus according to the first embodiment generates a blood flow image by the CFM method. Here, the ultrasonic diagnosis apparatus according to the first embodiment can execute various CFM methods in various manners of scanning as illustrated in FIG. 2A, FIG. 2B, and FIG. 2C. FIG. 2A, FIG. 2B, and FIG. 2C are diagrams for explaining manners of scanning in a variety of color flow mapping methods executed by the ultrasonic diagnosis apparatus according to the first embodiment.

In conventional color Doppler display, ultrasound transmission/reception is performed twice or more for one scan line. The CFM method performed in the conventional color Doppler display is referred to as "conventional CFM method." In the conventional CFM method, ultrasound transmission/reception is repeated in the same direction multiple times. Data (echo data) over multiple times forms one packet, and a closed process in a packet is performed to output one data (Doppler data) for each packet. When the number of scan lines in one frame is "M," the packet size corresponding to the number of times of transmission/reception per scan line is "N," and the pulse repetition frequency is "PRF," a frame rate "Fr" is expressed by the following Formula (1) in the conventional CFM method even when scan for B-mode is not performed.

$$Fr = \frac{PRF}{M \cdot N} \quad (1)$$

When "PRF=5000 (Hz), M=50, and N=10," the frame rate is 10 frame per second (fps) according to Formula (1). In other words, in the conventional CFM method, as the packet size "N" increases, the frame rate becomes slower.

FIG. 2A is a diagram illustrating a manner of scanning performed in the conventional CFM method, where "M=13, N=8." In the following, 13 scan lines illustrated in FIG. 2A, FIG. 2B, and FIG. 2C are denoted as L1 to L13 from the right to the left. In an example illustrated in FIG. 2A, the "1st, 2nd, . . . , 8th" ultrasound transmission/reception is performed on L1, the "9th, 10th, . . . , 16th" ultrasound transmission/reception is performed on L2, the "17th, 18th, . . . , 24th" ultrasound transmission/reception is performed on L3, and the "25th, 26th, . . . , 32nd" ultrasound transmission/reception is performed on L4. Then, in the example illustrated in FIG. 2A, the "33rd, 34th, . . . , 40th" ultrasound transmission/reception is performed on L5, the "41st, 42nd, . . . , 48th" ultrasound transmission/reception is performed on L6, the "49th, 50th, . . . , 56th" ultrasound transmission/reception is performed on L7, and the "57th, 58th, . . . , 64th" ultrasound transmission/reception is performed on L8. Ultrasound transmission/reception on L9 to L13 is performed similarly.

On the other hand, as a CFM method that improves the detection ability at low flow rates when compared with the conventional CFM method, a method called alternate scan has been put into practice. When the velocity of ultrasound is "C" and the reception center frequency is "$F_0$," "$V_{max}$" which is the maximum detectable flow rate that does not cause aliasing (aliasing velocity) is expressed by the following Formula (2).

$$V_{max} = \frac{C \cdot PRF}{4 f_0} \quad (2)$$

When a moving target indicator (MTI) filter having the same characteristics is used, the low flow rate detection ability is increased with lower aliasing velocity. In the alternate scan method, ultrasound transmission/reception is alternately performed in a block formed of a plurality of scan lines. When the number of scan lines (the raster number) in a block is "L," the time for data in all packets in a block to be output is "L" times that of the conventional CFM method. In the alternate scan method with the raster number "L," "$V_{max}$" is expressed by the following Formula (3).

$$V_{max} = \frac{C \cdot PRF}{4 f_0 L} \quad (3)$$

FIG. 2B is a diagram illustrating a manner of scanning performed in the alternate scan method, where "M=13, N=8, and L=4." In the alternate scan method with "N=8, L=4," ultrasound transmission/reception one time for each of four scan lines is alternately repeated eight times in four scan lines, whereby, in total, thirty-two transmission/reception of ultrasound is performed per block. For example, it is assumed that "L1 to L4" form "Block 1," and "L5 to L8" form "Block 2." In this case, in "Block 1," the 1st to 4th ultrasound transmission/reception is performed in order of "L1, L2, L3, L4," the 5th to 8th ultrasound transmission/reception is performed in order of "L1, L2, L3, L4," and finally, the 29th to 32nd ultrasound transmission/reception is performed in order of "L1, L2, L3, L4." In Block 2, the 33rd to 36th ultrasound transmission/reception is performed in order of "L5, L6, L7, L8," the 37th to 40th ultrasound transmission/reception is performed in order of "L5, L6, L7, L8," and finally, the 61st to 64th ultrasound transmission/reception is performed in order of "L5, L6, L7, L8."

It is noted that the frame rate is the same in the conventional CFM method and the alternate scan method if the values "PRF, M, N" are the same.

The reason why the frame rate is as expressed by Formula (1) will be described by explaining the processing actually performed in the conventional CFM method and the alternate scan method as described above. In the CFM method, data of blood flow components is extracted from echo data by removing the frequency components derived from the motion of tissues using the MTI filer. Then, in the CFM method, "velocity, distribution, power" are calculated from the extracted data by autocorrelation, and a two-dimensional distribution of the calculation results is displayed. In the conventional CFM method and the alternate scan method, transmission/reception is performed multiple times for the same raster.

A group of received data (echo data) at the same point on the same raster is called a packet. Then, the CFM processing unit 14a performs processing on the packet, examples of which processing include an MTI filter process, autocorrelation calculation, and "velocity, distribution, power estimation." Here, the size of a packet is generally "6 to 20." Finally, the CFM processing unit 14a generates a set of "velocity, distribution, power" data in a packet. The CFM processing unit 14a generates two-dimensional Doppler data by performing such processing in a two-dimensional space. For example, when three-dimensional scan is performed with a mechanical scan probe, the CFM processing unit 14a generates three-dimensional Doppler data by performing such processing in a two-dimensional space over multiple two-dimensional spaces. A blood flow image is thus displayed.

In this manner, in the conventional CFM method and the alternate scan method, a set of data is generated on a packet-by-packet basis. When the CFM method is performed, the ultrasound probe 1 also performs scan for B-mode for superimposing a blood flow image on a B-mode image. Because of those two reasons, the frame rate of blood flow is as slow as 5 to 30 fps. In the conventional CFM method and the alternate scan method, it is difficult to generate and display a blood flow image having the instantaneous blood flow behavior being extracted, because of such limited time resolution.

Then, a CFM method for improving the frame rate has been developed. This CFM method is hereinafter referred to as "high frame rate method." In the high frame rate method, ultrasound scanning is performed in a similar manner as in the scan for B-mode, rather than performing an MTI filter process, an autocorrelation calculation process, and a "velocity, distribution, power estimation" process on a packet-by-packet basis. In the high frame rate method, for example, as illustrated in FIG. 2C, ultrasound transmission/reception is performed one time for each of 13 scan lines (L1 to L13) that form a scan range in one frame. Then, in the high frame rate method, processing is performed in the frame direction for a data sequence at the same position in each frame. Accordingly, the high frame rate method can make the MTI filter process from processing data of a finite length, that is, a packet to processing data of an infinite length, thereby improving the performance of the MTI filter. At the same time, blood flow information can be displayed at the same frame rate as the scan frame rate. In other words, in the high frame rate, the MTI filter process can be an Infinite Impulse Response (IIR) filter process. Accordingly, in the high frame rate method, the frame rate is "N" times as high as that of Formula (1).

In this way, the ultrasonic diagnosis apparatus according to the first embodiment can execute the CFM method in various manners of scanning. For example, with the high frame rate method, the operator can observe the instantaneous blood flow behavior precisely with good time resolution by performing color Doppler display.

By contrast, in the FFT display with a single scan line, the time resolution is higher than that of the color Doppler display. The frequency analysis by FFT is an FFT process and more accurate than the frequency analysis by autocorrelation. Therefore, the FFT display is more suitable than the color Doppler display for observing the instantaneous blood flow behavior precisely with good time resolution. However, in the CWD method and the PWD method, correction (angular correction) is made by giving "θ" because when the angle between an ultrasound beam and the direction of a blood flow is "θ," the observed Doppler shift frequency has a value "cos θ" times as high as the true Doppler shift frequency.

However, in the FFT display, merely one-dimensional blood flow behavior, for example, on a scan line or in a sample volume at a point, is displayed. That is, the blood flow behavior that can be observed in the FFT display is blood flow behavior in a one-dimensional region of interest.

On the other hand, in the color Doppler display, the blood flow behavior can be displayed in a two-dimensional space. In a case where three-dimensional scan is performed, in the color Doppler display, the blood flow behavior can be displayed in a three-dimensional space. However, in the color Doppler display, the frame rate is not as high enough as that of the FFT display as described above. In addition, when angular correction is made two-dimensionally or three-dimensionally, the operator has to set "θ" for each place, and therefore, the angular correction is generally not performed in the color Doppler display.

For those reasons, the color Doppler display is used to observe the blood flow behavior in a two-dimensional or three-dimensional region of interest and cannot serve as a substitute for the FFT display. However, as described above, the blood flow behavior that can be observed with the FFT display is blood flow behavior in a one-dimensional region of interest. In order to observe the blood flow behavior in a two-dimensional or three-dimensional region of interest, for example, it is necessary to set a plurality of sample volumes in a two-dimensional space or a three-dimensional space and to collect a Doppler spectrum by the PWD method for each of a plurality of sample volumes.

Then, in the first embodiment, in order to observe the blood flow behavior in a two-dimensional or three-dimensional region of interest precisely with good time resolution, the following process is performed. Specifically, the CFM processing unit 14a acquires two-dimensional or three-dimensional blood flow information in time sequence in a scan range formed of a plurality of scan lines, from the two-dimensional or three-dimensional echo data collected through ultrasound transmission/reception performed in the scan range. More specifically, the CFM processing unit 14a acquires two-dimensional or three-dimensional blood flow information in time sequence in a scan range by autocorrelation. The image generator 15a generates blood flow images in time sequence from the two-dimensional or three-dimensional blood flow information in time sequence in the scan range. The detector 15b detects movement information in time sequence of speckles in a preset two-dimensional or three-dimensional region of interest, among the blood flow images in time sequence. The controller 17 controls the monitor 2 to display movement information data that is data based on the movement information in time sequence.

An example of the process described above will be described in detail below. In the case described below, the transmitter/receiver 11 executes ultrasound transmission/reception in a manner of scanning by the high frame rate method, and the CFM processing unit 14a acquires blood flow information based on the high frame rate method. More specifically, in the following description, the CFM processing unit 14a acquires two-dimensional or three-dimensional blood flow information in time sequence in a scan range, from two-dimensional or three-dimensional echo data collected in a manner of scanning in which ultrasound transmission/reception in a scan range is performed once for each scan line. However, in the first embodiment, the conventional CFM method or the alternate scan method as described above may be executed, for example, if the frame rate can be as high as 60 fps or higher, depending on the size of the scan range.

Figure 3:
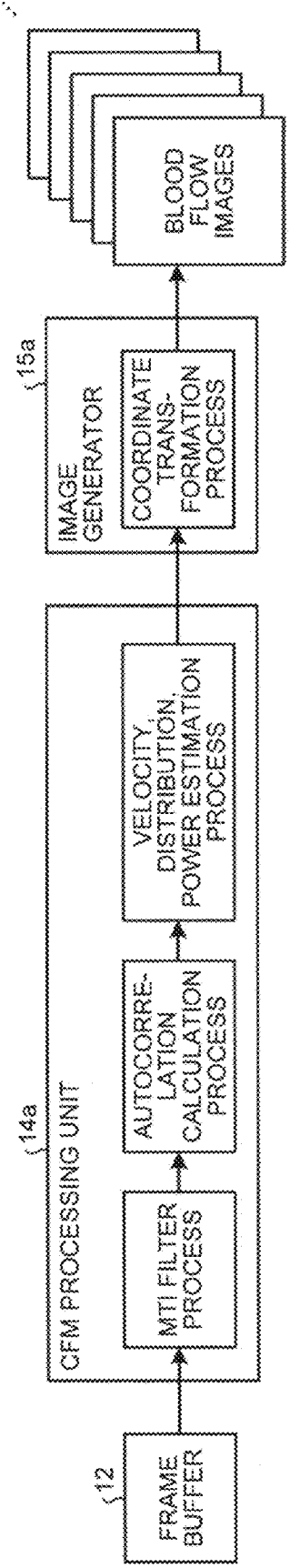
FIG. 3 is a diagram for explaining an example of processing in a CFM processing unit according to the first embodiment.

First, the CFM processing unit 14a reads out, from the frame buffer 12, two-dimensional or three-dimensional echo data collected through ultrasound transmission/reception performed in a scan range formed of a plurality of scan lines. Then, the CFM processing unit 14a acquires two-dimensional or three-dimensional blood flow information in time sequence in the scan range by performing autocorrelation on the two-dimensional or three-dimensional echo data. For example, based on the scan sequence designated by the controller 17, the transmitter/receiver 11 controls the ultrasound probe 1 to execute a manner of scanning by the high frame rate method in which ultrasound transmission/reception in the two-dimensional scan range is performed once for each scan line, and the echo signal of one frame is received. Accordingly, the transmitter/receiver 11 generates two-dimensional echo data and stores them in the frame buffer 12. The CFM processing unit 14a acquires two-dimensional blood flow information in time sequence in the scan range by performing autocorrelation on the two-dimensional echo data. Here, the blood flow information is the velocity, distribution, and power of blood flow. FIG. 3 is a diagram for explaining an example of processing in the CFM processing unit and the image generator according to the first embodiment.

As illustrated in FIG. 3, the processing in the CFM processing unit 14a includes three blocks, namely, an "MTI filter process," an "autocorrelation calculation process," and a "velocity, distribution, power estimation process." In the "MTI filter process" block illustrated in FIG. 3, for example, a fourth order IIR filter is used as an MTI filter.

Here, it is assumed that the echo data at "a certain position" in the current frame "the n-th frame" is "x(n)," the echo data in the immediately preceding frame "the (n−1)th frame" at the same position is "x(n−1)," and the echo data in "the (n−2)th frame", which is two frames preceding the current frame at the same position, is "x(n−2)." Then, the echo data in "the (n−3)th frame", which is three frames preceding the current frame at the same position, is "x(n−3)," and the echo data in "the (n−4)th frame", which is four frames preceding the current frame at the same position, is "x(n−4)." The filter coefficient of the MTI filter is "$a_k$" and "$b_k$." In this case, "y(n)" which is a blood flow component of "x(n)" output from the "MTI filter process" block is expressed by the following Formula (4).

$$y(n) = \sum_{k=0}^{4} b_k x(n-k) - \sum_{k=1}^{4} a_k y(n-k) \tag{4}$$

The output result from the "MTI filter process" block is input to the "autocorrelation calculation process" block illustrated in FIG. 3. In the "autocorrelation calculation process" block, autocorrelation values of lag 0 and lag 1 are calculated. When lag 0 is "C0(n)" and lag 1 is "C1(n)," "C0(n)" is calculated by the following Formula (5), and "C1(n)" is calculated by the following Formula (6).

$$C0(n) = \sum_{k=0}^{N-1} x^*(n-k)x(n-k) \tag{5}$$

$$C1(n) = \sum_{k=0}^{N-1} x^*(n-k-1)x(n-k) \tag{6}$$

In the expressions (5) and (6), the asterisk subscript "*" represents a complex conjugate, and "N" represents an addition range in the frame direction that is set in the autocorrelation calculation. "C0(n)" is equivalent to power. Although not illustrated in FIG. 3, the signal-to-noise ratio (S/N) can be increased at the expense of distance resolution by performing smoothing, such as moving average, in the ultrasonic beam direction for lag 0 and lag 1 obtained from the expressions (5) and (6).

The output result from the "autocorrelation calculation process" block is input to the "velocity, distribution, power estimation process" block illustrated in FIG. 3. In the "velocity, distribution, power estimation process" block, the velocity "V" of blood flow, the distribution "T" of velocity of blood flow" and the power "P" of blood flow at "a certain position" in "the n-th frame" are calculated from "C0(n)" and "C1(n)" according to the following Formula (7).

$$\left.\begin{array}{l} V = a\tan 2(imag(C1), real(C1)) \\ P = C0 \\ T = \dfrac{1 - |C1|}{C0} \end{array}\right\} \tag{7}$$

In the first equation in Formula (7), "a tan 2" is an "arc tangent function" that outputs the angles "−π to +π," "image" is a function that outputs only an imaginary number part from a complex number, and "real" is a function that outputs only a real number part from a complex number. In other words, in the first equation in Formula (7), a change in phase of the imaginary number part and the real number part of "C1(n)" is calculated as the velocity "V" of blood flow. In this way, the power is obtained as lag 0 by autocorrelation calculation, and the velocity and the distribution are obtained by frequency-analyzing the result of the autocorrelation calculation.

Through the process as described above, the CFM processing unit 14a acquires blood flow information for each of a plurality of points set on each scan line in a scan range, frame by frame, and outputs the blood flow information to the image generator 15a. The image generator 15a generates blood flow images in time sequence from the two-dimensional or three-dimensional blood flow information in time sequence in the scan range. In the first embodiment, the image generator 15a generates blood flow images in time sequence from the two-dimensional blood flow information. Specifically, the image generator 15a generates two-dimensional blood flow images in time sequence from the two-dimensional blood flow information in time sequence by performing a "coordinate transformation process" as illustrated in FIG. 3.

For example, the image generator 15a generates a power image in grayscale in which power values are imaged in grayscale. Alternatively, the image generator 15a generates a color power image in which, using only the signs of velocity as directions, the lightness of red is changed with power values at positions with the plus sign, and the lightness of blue is changed with power values at positions with the minus sign, for example. Alternatively, the image generator 15a generates a color power image in which the velocity and the power are transformed with a two-dimensional map. The image generator 15a may generate not only blood flow images for power display but also blood flow images for velocity display and/or blood flow images for velocity distribution display. It is noted that the image generator 15a according to the first embodiment generates a blood flow image for power display even when only velocity display or velocity distribution display is requested, because the blood flow image used in the processing in the detector 15b described below is preferably a blood flow image for power display.

The detector 15b illustrated in FIG. 1 detects movement information in time sequence of speckles in a preset two-dimensional or three-dimensional region of interest among blood flow images in time sequence. Specifically, the detector 15b detects movement information in time sequence for each of a plurality of points in the region of interest. First, an example of the setting of the region of interest will be described.

For example, the controller 17 controls the monitor 2 to display one of the blood flow images generated by the image generator 15a, based on a request for ROI setting by the operator. The operator refers to the monitor 2 and uses the input device 3 to set the region of interest in which the operator wishes to observe the blood flow behavior. In a case where a two-dimensional blood flow image is generated and displayed, the operator sets a two-dimensional region of interest. In a case where a three-dimensional blood flow image is generated and a cross section of the three-dimensional blood flow image is displayed, the operator sets a two-dimensional region of interest. Alternatively, in a case where a three-dimensional blood flow image is generated, and, for example, orthogonal three cross sections of the three-dimensional blood flow image are displayed, the operator sets a two-dimensional region of interest in each section thereby setting a three-dimensional region of interest. In the first embodiment, the case where the operator sets a two-dimensional region of interest for a two-dimensional blood flow image will be described. FIG. 4, FIG. 5, FIG. 6A, and FIG. 6B are diagrams for explaining an example of processing in the detector according to the first embodiment.

Figure 4:
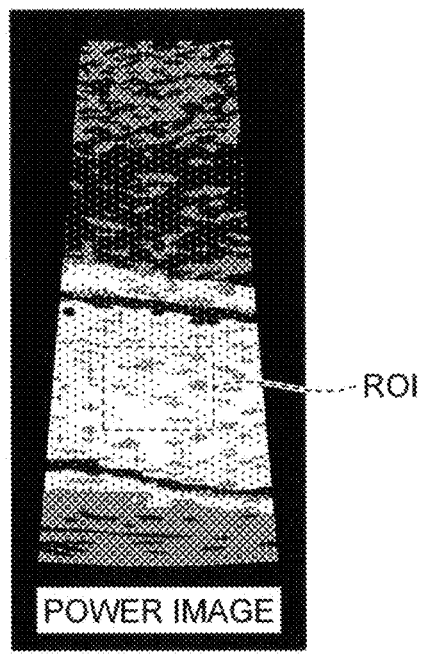
FIG. 4, FIG. 5, FIG. 6A, and FIG. 6B are diagrams for explaining examples of processing in a detector according to the first embodiment.

For example, as illustrated in FIG. 4, the operator sets a rectangular ROI for a grayscale power image. In the first embodiment, the ROI can be set in any shape. In the first embodiment, the ROI used in the processing in the detector 15b may be set on a B-mode image in a scan range including the scan range for color Doppler display.

Figure 5:
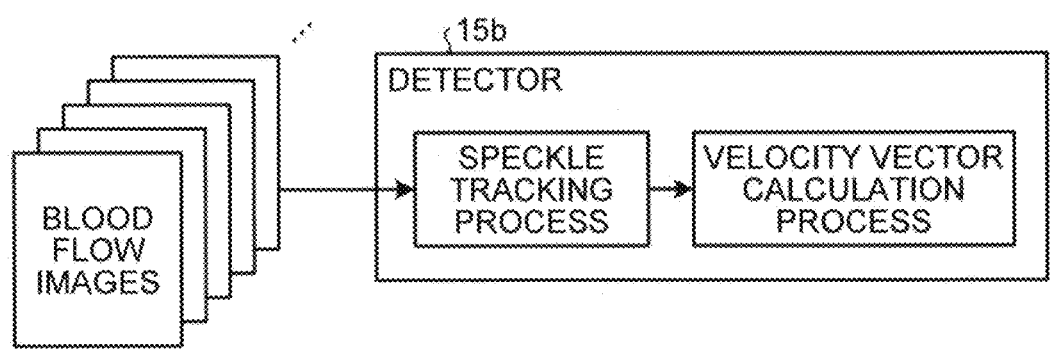

Then, as illustrated in FIG. 5, the detector 15b mainly performs two processes, namely, a "speckle tracking process" and a "velocity vector calculation process." In the "speckle tracking process" block, the detector 15b calculates motion vectors at a plurality of points in the ROI by performing speckle tracking by cross-correlation between continuous frames or between frames separated from each other by a few frames. Then, in the "velocity vector calculation process" block, the detector 15b converts the motion vectors into velocity vectors using a frame-to-frame time difference.

Figure 6A:
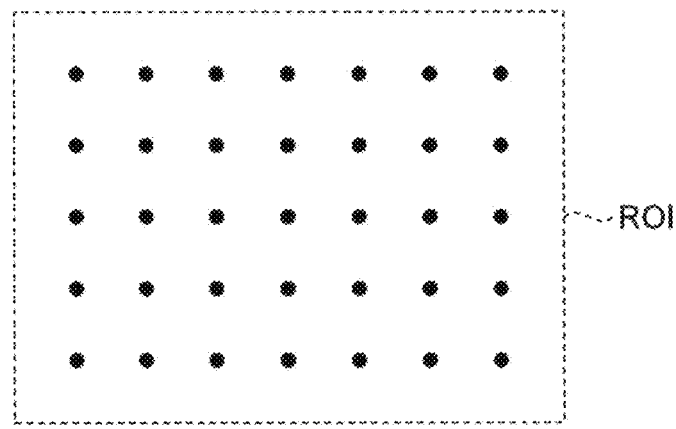
Figure 6B:
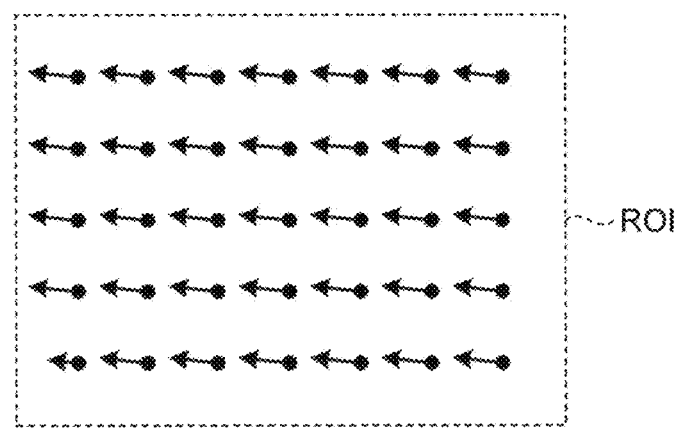

For example, as illustrated in FIG. 6A, it is assumed that 35 tracking points are set in the ROI. The detector 15b calculates a motion vector by tracking which position the speckle at the tracking point in "the (n−1)th frame" moves to in "the n-th frame." Then, in the "velocity vector calculation process" illustrated in FIG. 5, the detector 15b calculates a velocity vector from the motion vector using the frame-to-frame time difference between the two frames that are targets of the cross-correlation process. For example, as illustrated in FIG. 6B, the detector 15b calculates the velocity vector for each of 35 points in the ROI in "the n-th frame." The detector 15b calculates the velocity vectors in time sequence for each of a plurality of points in the ROI by repeatedly performing the process above among blood flow images.

Here, if reflectors far smaller than the spectrum of the transmitted ultrasonic wave are densely populated, the echo signals interfere with each other. The magnitude of interference is the magnitude of amplitude of the echo signal, and a speckle, which is a point-like artifact, appears in the ultrasound image based on such amplitude information. The power image is a blood flow image in which power values representing the degree of the quantity of blood as reflectors are imaged. Therefore, the velocity vector converted from the movement vector of the speckle of the power image is information corresponding to the velocity vector of the blood flow. In other words, in the first embodiment, the velocity vector based on the speckle in each of a plurality of points in the ROI of the blood flow image having the power information is "movement information" representing the blood flow behavior.

The controller 17 controls the monitor 2 to display movement information data that is data based on the movement information in time sequence. The movement information data displayed under the control of the controller 17 according to the first embodiment will be specifically described below mainly using FIG. 7 to FIG. 10. FIG. 7 to FIG. 10 are diagrams for explaining specific examples of the movement information data displayed by the controller according to the first embodiment.

Figure 7A:
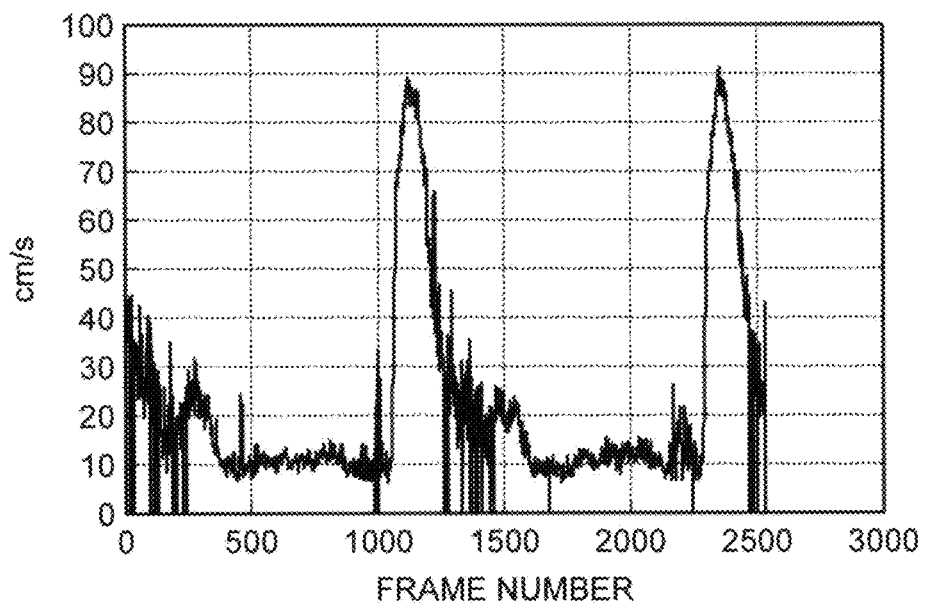
Figure 7B:
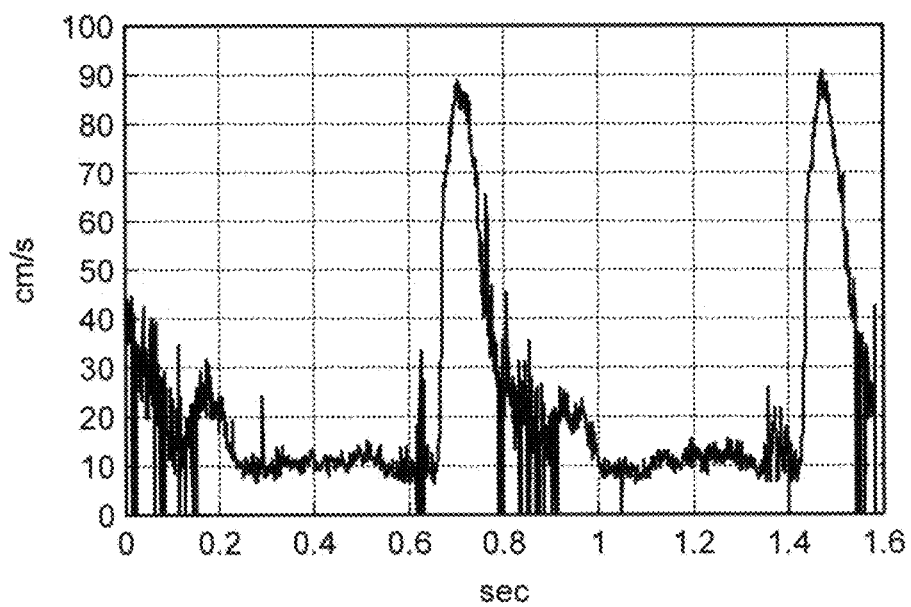

Specifically, the controller 17 controls the image generator 15a to generate, as movement information data, a temporal change curve in which the representative values of movement information in time sequence for each of a plurality of points are plotted in time sequence. The controller 17 then controls the monitor 2 to display the temporal change curve. The representative value of the movement information is the average velocity. Here, the average velocity that is the representative value is, for example, the mean value of the scalar quantity of the velocity vector for each of a plurality of points. FIG. 7A illustrates an example in a case where the image generator 15a generates an average velocity temporal change curve in which the horizontal axis represents the frame number and the vertical axis represents the average velocity (unit: cm/s). FIG. 7B is an example in a case where the image generator 15a generates an average velocity temporal change curve in which the horizontal axis represents the time (unit: sec) converted from the frame number using the frame-to-frame time difference and the vertical axis represents the average velocity (unit: cm/s). The information used in the horizontal axis is any parameter that can be changed by the operator.

The average velocity as the representative value may be calculated either by the detector 15b or by the controller 17. In the first embodiment, the average velocity as the representative value may be the mean value of the scalar quantity of the setting direction component of the velocity vector for each of a plurality of points. The setting direction component is, for example, the lateral direction, the depth direction, or the direction in which the blood vessel runs.

The average velocity as the representative value may be the scalar quantity of the average velocity vector or the scalar quantity of the setting direction component of the average velocity vector. The setting direction component is, for example, the lateral direction, the depth direction, of the direction in which the blood vessel runs.

The representative value may be the maximum flow rate. The maximum flow rate as the representative value is the maximum value of the scalar quantity of the velocity vector or the maximum value of the scalar quantity of the setting direction component of the velocity vector. The setting direction component is, for example, the lateral direction, the depth direction, or the direction in which the blood vessel runs.

The representative value may be the median of the flow rate. The median as the representative value is the median of the scalar quantity of the velocity vector or the median of the scalar quantity of the setting direction component of the velocity vector. The setting direction component is, for example, the lateral direction, the depth direction, or the direction in which the blood vessel runs.

The representative value may be a variance. The variance as the representative value is the variance of the scalar quantity of the velocity vector or the variance of the scalar quantity of the setting direction component of the velocity vector. The setting direction component is, for example, the lateral direction, the depth direction, or the direction in which the blood vessel runs.

The representative value may be a value in the section with the greatest frequency or "the n-th highest frequency" in the histogram of the scalar quantity of the velocity vector for each of a plurality of points. For example, in a case where the section "50 cm/s to 60 cm/s" includes the greatest frequency, the representative value may be "55 cm/s." Alternatively, the representative value may be calculated from the section with "the third highest frequency" in order to avoid calculation of the representative value from the section with the greatest frequency due to noise. When the representative value is calculated from the histogram, the histogram of the scalar quantity of the setting direction component of the velocity vector for each of a plurality of points may be used. The setting direction component is, for example, the lateral direction, the depth direction, or the direction in which the blood vessel runs.

When a plurality of representative values are selected from a variety of representative values described above, the controller 17 controls the image generator 15a to generate a temporal change curve for each of the selected representative values and controls the monitor 2 to display the temporal change curve.

Figure 8A:
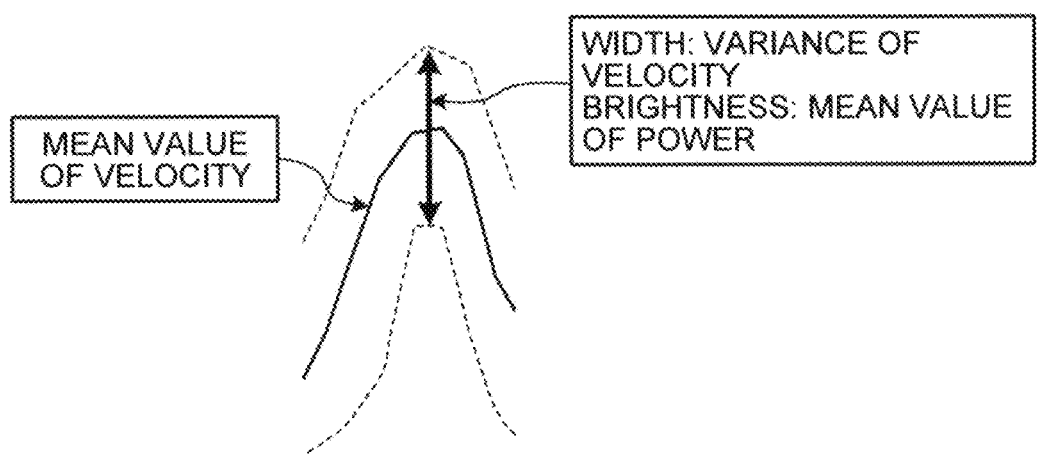

Here, the temporal change curve of the average velocity illustrated in FIG. 7A or FIG. 7B is similar to the Doppler spectrum and therefore can be used in place of the FFT display. Then, the controller 17 may control the image generator 15a to generate, as the movement information data, a temporal change image in which the temporal change curve is imaged. Specifically, as illustrated in FIG. 8A, the image generator 15a generates a temporal change curve (see the solid line in the figure) in which the mean value of the velocity in the ROI that is calculated from the velocity vector is plotted, and sets the width in the vertical axis direction in accordance with the variance of the velocity in the ROI (see the dotted line in the figure). Then, as illustrated in FIG. 8A, the image generator 15a generates a temporal change image by setting the brightness of the line in which the mean value of the velocity is at the center and the length in the vertical axis direction is the variance of the velocity, in accordance with the mean value of the power in the ROI.

Figure 8B:
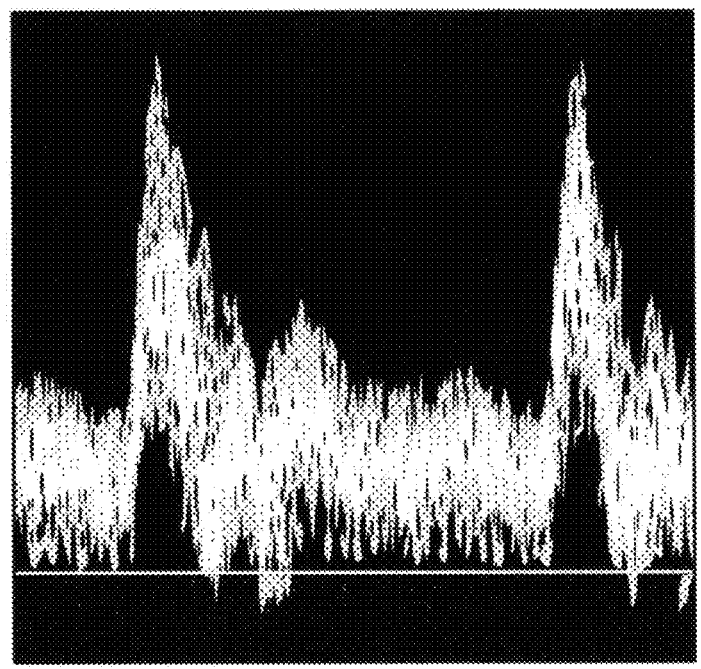

Accordingly, the image generator 15a generates a temporal change image illustrated in FIG. 8B, and the controller 17 controls the monitor 2 to display the temporal change image. The temporal change image of the average velocity illustrated in FIG. 8B is an image more similar to a Doppler spectrum than the temporal change curve of the average velocity.

Figure 9:
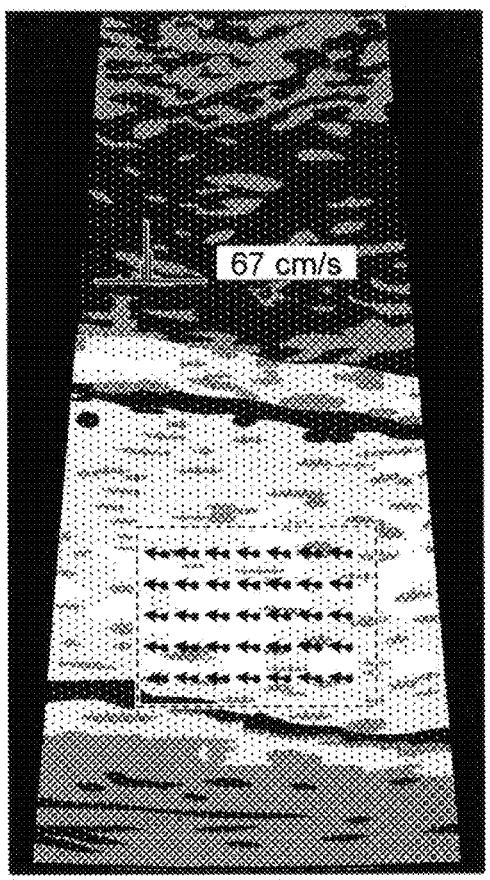

Alternatively, the controller 17 controls the image generator 15a to generate, as the movement information data, a superimposed image in which predetermined graphics showing the movement information of each of a plurality of points is superimposed in the region of interest of the blood flow image. For example, as illustrated in FIG. 9, the image generator 15a generates a superimposed image in which arrows representing the respective velocity vectors at a plurality of points are superimposed in the ROI of the power image.

Alternatively, the controller 17 may also controls the image generator 15a to generate, as the movement information data, an image in which at least one of the representative value and the histogram representing the distribution of values of movement information at a plurality of points from which the representative value is calculated is superimposed at a predetermined position of the superimposed image. For example, as illustrated in FIG. 9, the image generator 15a combines the average velocity "67 cm/s" as the representative value on the upside to the RIO in the superimposed image. In addition, for example, as illustrated in FIG. 9, the image generator 15a combines, on the left side to the representative value, the histogram representing the distribution of the scalar quantity of the velocity vector at each of the 35 tracking points from which the average velocity is calculated. The positions where the representative value and the histogram are combined may not be on the superimposed image but be on the upside to the superimposed image.

Here, a plurality of blood flow images are generated in time sequence and therefore can be displayed in motion. The arrow superimposed in the ROI of the power image is an arrow representing the velocity vector at each of a plurality of points that is calculated in the power image. The representative value and the histogram additionally superimposed on the superimposed image are the representative value and the histogram in the ROI of the power image corresponding to the superimposed image. In other words, a plurality of superimposed images and a plurality of superimposed images with the representative value and the histogram superimposed thereon are generated and thus can be displayed in motion as well.

Then, in the case where the superimposed images are to be displayed in motion concurrently with the temporal change curve or the temporal change image, the controller 17 controls to display the position corresponding to the time phase of the displayed superimposed image, in the temporal change curve or the temporal change image. For example, the controller 17 performs display control illustrated in FIG. 10 in the case where the superimposed images with the representative value and the histogram superimposed thereon are displayed in motion concurrently with the temporal change curve of the average velocity illustrated in FIG. 7A.

Specifically, as illustrated in FIG. 10, the controller 17 controls to combine and display a line marker a showing the position at a point of time when the average velocity is calculated in the superimposed image displayed on the monitor 2, onto the temporal change curve of the average velocity. Here, the position of the line marker a illustrated in FIG. 10 moves from the left to the right in accordance with the frame of the displayed blood flow image. In the first embodiment, in the case where color Doppler images for velocity display or velocity distribution display are displayed in motion concurrently with the temporal change curve or the temporal change image, the controller 17 may control to display the position corresponding to the time phase of the displayed blood flow image in the temporal change curve or the temporal change image.

In the example described above, a variety of movement information data based on movement information detected in a two-dimensional ROI is displayed. However, in the first embodiment, a variety of movement information data based on movement information detected in a three-dimensional ROI may be displayed.

Figure 11:
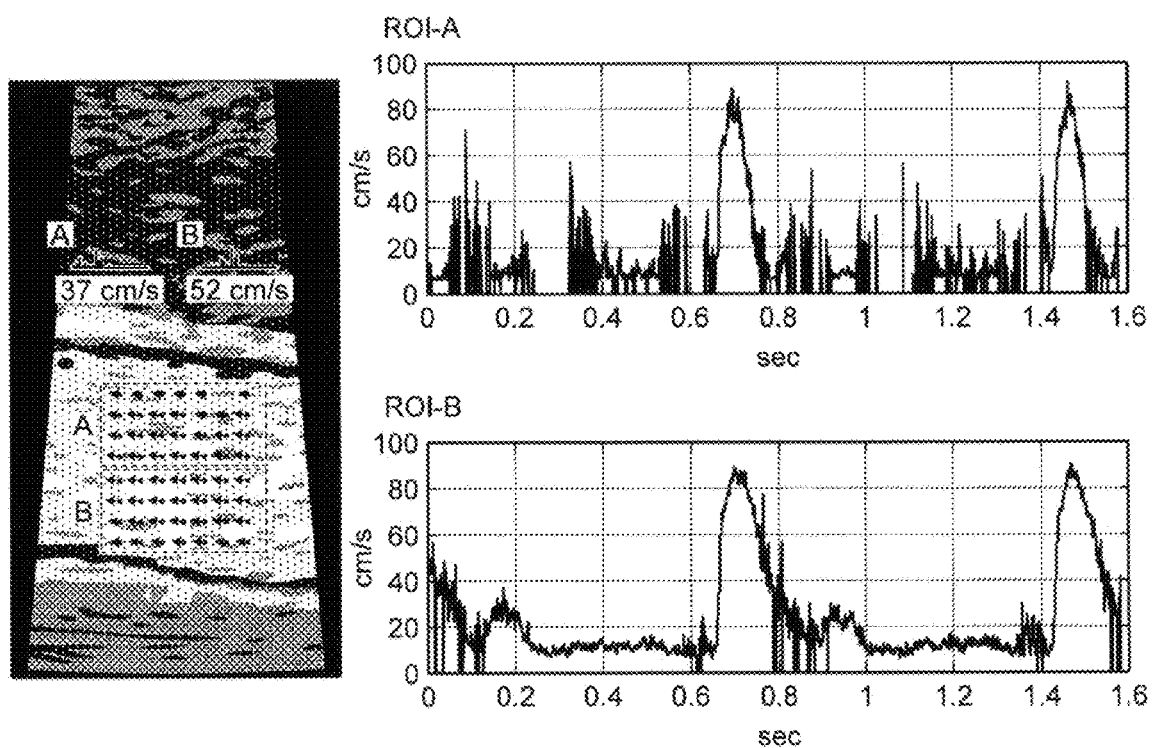
FIG. 11 is a diagram for explaining an example of movement information data displayed when a plurality of regions of interest are set in the first embodiment.

The operator can set a two-dimensional ROI at any position since the blood flow image is a two-dimensional image. In the case where the blood flow image is captured three-dimensionally, the blood flow image is two-dimensionally displayed in any given cross section in the captured space, so that the operator can set a two-dimensional or three-dimensional ROI at any place. Therefore, according to the first embodiment, a plurality of ROIs may be set. In the case where a plurality of ROIs are set, the detector 15b and the image generator 15a perform the processing for each of a plurality of ROIs concurrently under the control of the controller 17. FIG. 11 is a diagram for explaining an example in which the movement information data is displayed when a plurality of regions of interest are set in the first embodiment.

For example, when the operator wishes to observe the blood flow behavior in the ROI illustrated in FIG. 6 in more details, the operator sets an ROI-A and an ROI-B by dividing the ROI illustrated in FIG. 6 into two as illustrated in FIG. 11. In this case, the detector 15b calculates the velocity vector for each of a plurality of points in the ROI-A and the velocity vector for each of a plurality of points in the ROI-B. Then, for example, the image generator 15a generates a temporal change curve of the average velocity for each of the ROI-A and the ROI-B, as illustrated in FIG. 11. In the temporal change curves for the ROI-A and the ROI-B illustrated in FIG. 11, the horizontal axis represents "time (unit: sec)."

Then, as illustrated in FIG. 11, the image generator 15a superimposes, on the power image, arrows representing the velocity vectors at a plurality of points in the ROI-A and arrows representing the velocity vectors at a plurality of points in the ROI-B. In addition, as illustrated in FIG. 11, the image generator 15a superimposes the average velocity and the histogram of the velocity in the ROI-A and the average velocity and the histogram of the velocity in the ROI-B. Then, as illustrated in FIG. 11, the image generator 15a generates a composite image in which the superimposed image having information of two ROIs superimposed on the same power image is combined with the two temporal change curves. Such a composite image is displayed on the monitor 2 by the controller 17. Although not illustrated in FIG. 11, in the case where the superimposed images are displayed in motion, the line markers each representing the position corresponding to the time phase of the displayed superimposed image may be combined with the two temporal change curves.

The setting of the kind of the movement information data and the display manner in the case where multiple kinds of movement information data are set may be set in advance by the operator or may be initially set.

Figure 12:
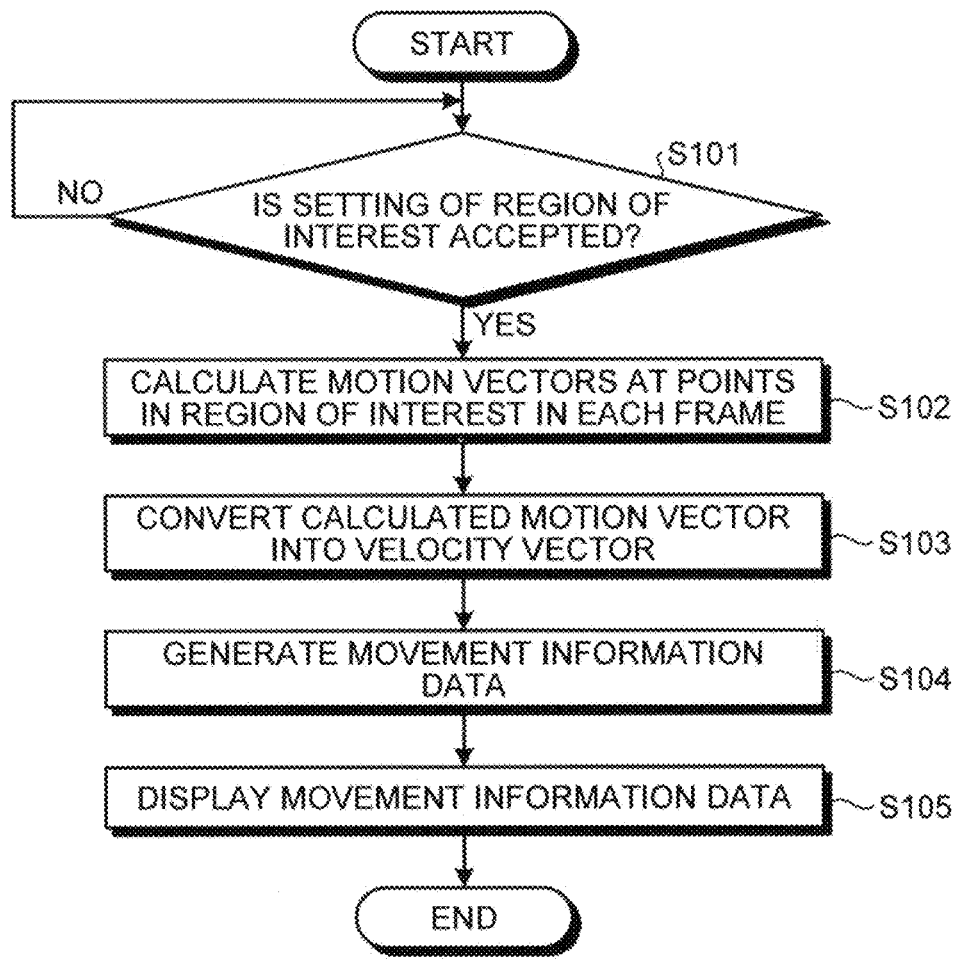
FIG. 12 is a flowchart for explaining processing in the ultrasonic diagnosis apparatus according to the first embodiment.

Next, using FIG. 12, the processing in the ultrasonic diagnosis apparatus according to the first embodiment will be described. FIG. 12 is a flowchart for explaining the processing in the ultrasonic diagnosis apparatus according to the first embodiment. In FIG. 12, the ROI is set after collection of blood flow images, and the processing in the detector 15b and the controller 17 described above is performed concurrently during cine replay of blood flow images after collection of blood flow images.

As illustrated in FIG. 12, the controller 17 of the ultrasonic diagnosis apparatus according to the first embodiment determines whether the setting of a region of interest is accepted from the operator (Step S101). Here, if the setting of a region of interest is not accepted (No at Step S101), the controller 17 waits until the setting of a region of interest is accepted.

On the other hand, if the setting of a region of interest is accepted (Yes at Step S101), the controller 17 notifies the detector 15b of the positional information of the region of interest, and the detector 15b calculates motion vectors at a plurality of points in the region of interest in each frames (Step S102) and converts the calculated motion vectors into velocity vectors (Step S103).

Then, the image generator 15a generates movement information data such as a temporal change curve with a line marker, a temporal change image with a line marker, or a superimposed image, under the control of the controller 17 (Step S104). Then, the monitor 2 displays the movement information data under the control of the controller 17 (Step S105). The process then ends.

It has been described in the first embodiment that the ROI is set after collection of blood flow images, and the processing in the detector 15b and the controller 17 described above is performed during cine replay of blood flow images after collection of blood flow images. However, in the first embodiment, the ROI may be set before collection of blood flow images, and the processing in the detector 15b and the controller 17 described above may be performed in real time concurrently with collection of blood flow images.

As described above, in the first embodiment, the velocity vector in the ROI set in the blood flow image is detected, and information of the detected velocity vector is displayed in the form of a temporal change curve, a temporal change image, a superimposed image, etc. In other words, in the first embodiment, information similar to the information about the one-dimensional blood flow behavior as observed in Doppler display can be displayed two-dimensionally or three-dimensionally by setting an ROI in any shape at any position in the blood flow image. Therefore, in the first embodiment, the blood flow behavior in the two-dimensional or three-dimensional region of interest can be observed precisely with good time resolution. In addition, in the first embodiment, a plurality of regions of interest can be set. Therefore, in the first embodiment, the blood flow behavior in a plurality of two-dimensional or three-dimensional regions of interest can be observed at the same time. It is noted that the blood flow information may only include the power obtained by auto-correlation calculation with lag 0, because it is preferred that the detection of the movement information be targeted for a power image. In other words, in the first embodiment, the CFM processing unit 14a may acquire only power by auto-correlation, and the image generator 15a may generate only power images in time sequence.

In a second embodiment, a Doppler spectrum separately generated through scan for Doppler display is displayed along with the movement information data explained in the first embodiment.

In the second embodiment, the PWD processing unit 14b acquires blood flow information in time sequence in a sample volume on a scan line by performing frequency analysis, for example, by fast fourier transform, on echo data collected through ultrasound transmission/reception separately performed on the scan line included in the region of interest as explained in the first embodiment. Then, in the second embodiment, the image generator 15a generates a Doppler spectrum from the blood flow information in time sequence that is acquired through frequency analysis.

Figure 13:
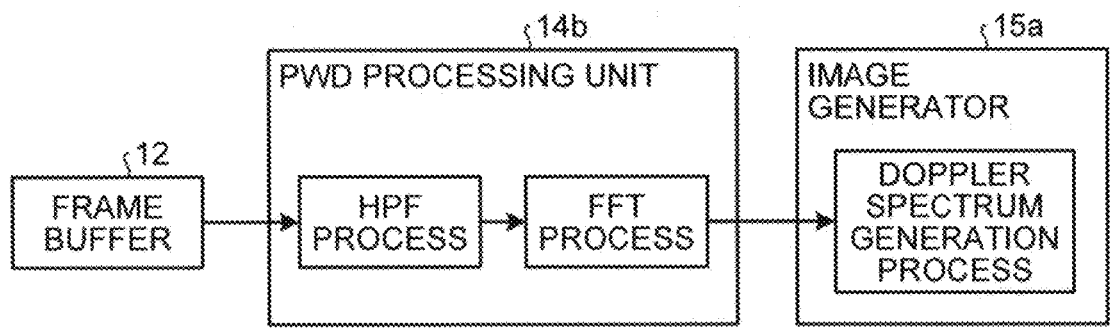
FIG. 13 is a diagram for explaining processing in a PWD processing unit and an image generator in Doppler spectrum generation.

First, the PWD processing unit 14b reads out one-dimensional echo data corresponding to the position of the sample volume on the scan line, among one-dimensional echo data generated through pulsed wave transmission/reception, from the frame buffer 12. Alternatively, the transmitter/receiver 11 may store only one-dimensional echo data corresponding to the position of the sample volume on the scan line into the frame buffer 12 using a short time gate, and the PWD processing unit 14b may read out the one-dimensional echo data corresponding to the position of the sample volume on the scan line. FIG. 13 is a diagram for explaining processing in the PWD processing unit and the image generator in Doppler image generation.

First, in an "HPF process" block illustrated in FIG. 13, the PWD processing unit 14b removes low frequency components (clutter) and extracts blood flow components by performing a high pass filter (HPF) process with the characteristics similar to those of the MTI filter on the one-dimensional echo data. Then, in an "FFT process" block illustrated in FIG. 13, the PWD processing unit 14b calculates blood flow information (velocity, distribution, power) from the blood flow components by fast fourier transform. In the "FFT process" block illustrated in FIG. 13, the angular correction as described above is also performed. Then, in a "Doppler spectrum generation process" block illustrated in FIG. 13, the image generator 15a generates a Doppler spectrum.

Figure 14:
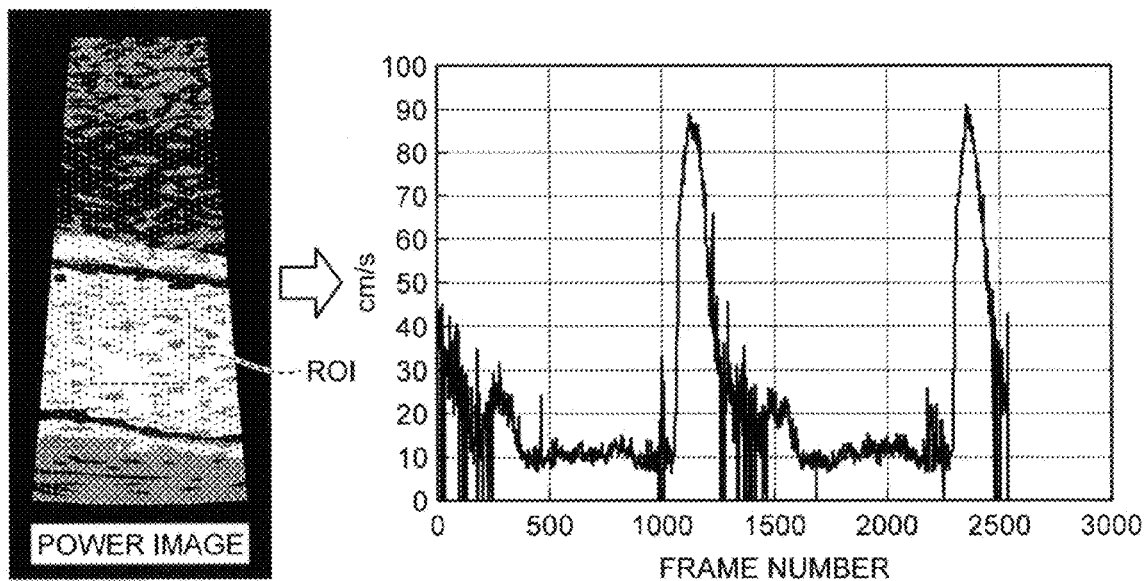

FIG. 14 to FIG. 17 are diagrams for explaining an example of a process procedure executed by an image processor according to the second embodiment. For example, in a similar manner as in the first embodiment, in the second embodiment, as illustrated in FIG. 14, an ROI is set in a power image. Then, in the second embodiment, the image generator 15a generates, for example, movement information data such as a temporal change curve of the average velocity using the processing result from the detector 15b, as illustrated in FIG. 14.

Figure 15:
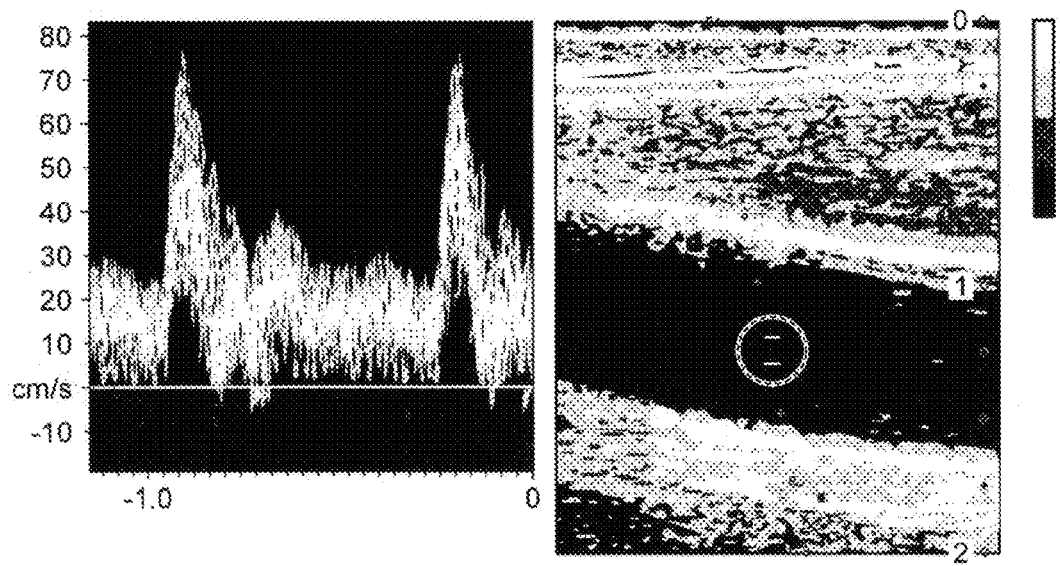

In addition, in the second embodiment, for example, a sample volume included in the ROI is set on a B-mode image shown in the diagram on the right in FIG. 15 (see the dotted line in the figure). Then, in the second embodiment, scan for Doppler display is performed at a time different from when the blood flow image is captured, on the scan line on the sample volume. Accordingly, the image generator 15a generates a Doppler spectrum illustrated in the diagram on the left in FIG. 15.

Figure 16:
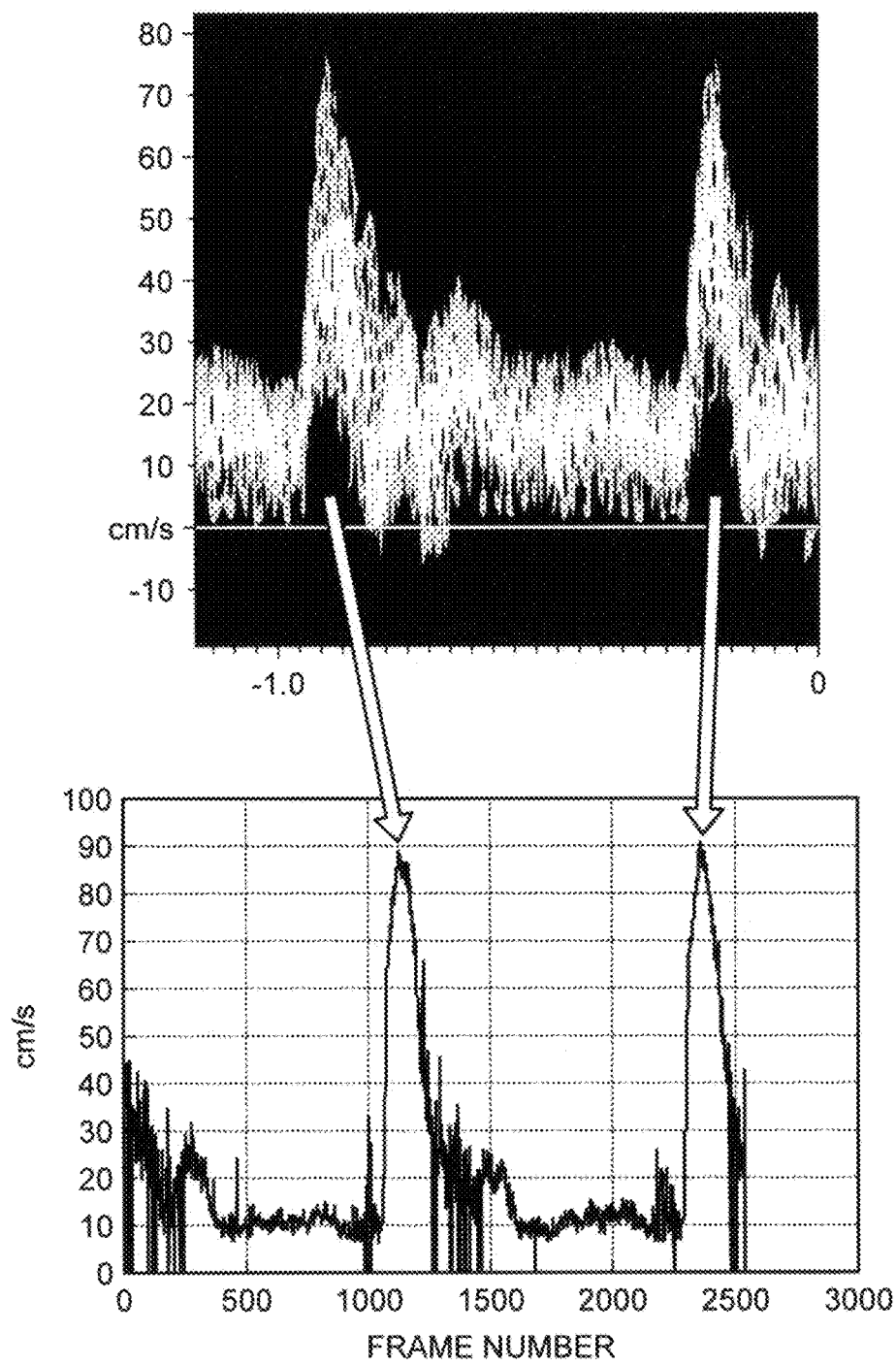

Then, the controller 17 according to the second embodiment controls the monitor 2 to display the Doppler spectrum and the movement information data in a manner in which the same time phase in both data is explicitly shown. For example, in a case where the Doppler spectrum and the temporal change curve are concurrently displayed, as illustrated in FIG. 16, the controller 17 determines that the time when the waveform has a peak in the Doppler spectrum and the time when the representative value has a peak in the temporal change curve correspond to almost the same time phase. For example, as illustrated in FIG. 16, the controller 17 controls to display an arrow that connects those peaks so that the operator can easily visually recognize the time phase when those peaks form. Alternatively, for example, the controller 17 changes the display scale of the horizontal axis of the Doppler spectrum or change the display scale of the horizontal axis of the temporal change curve so that the time phases when the peaks form are approximately matched in the direction of the horizontal axis.

In a case where the superimposed images are displayed in motion concurrently with the Doppler spectrum, the controller 17 according to the second embodiment controls to display the position corresponding to the time phase in the displayed superimposed image, in the Doppler spectrum. In a case where the superimposed images are displayed in motion concurrently with the Doppler spectrum and the temporal change curve, the controller 17 according to the second embodiment controls to display the position corresponding to the time phase in the displayed superimposed image, in the Doppler spectrum and the temporal change curve.

For example, in the case where the superimposed images having the average velocity as the representative value and the histogram superimposed thereon are displayed in motion concurrently with the Doppler spectrum and the temporal change curve of the average velocity, as illustrated in FIG. 17, the controller 17 controls to combine a line marker a showing the position at a point of time when the average velocity is calculated in the superimposed image displayed on the monitor 2, onto the temporal change curve of the average velocity, in a similar manner as in the first embodiment. In addition, as illustrated in FIG. 17, the controller 17 controls to combine a line marker b showing the position at a point of time when the average velocity is calculated in the superimposed image displayed on the monitor 2, onto the Doppler spectrum. The line marker a and the line marker b move simultaneously with progress of replay of the superimposed images.

The movement information data to be combined with the line marker may be a temporal change image. The process for matching the time phases may be performed using peaks as described above or may be performed, for example, using information of electrocardiograph (ECG) if ECG is collected concurrently with data collection.

In the second embodiment, if the region of interest including almost the entire scan line on which a continuous wave is transmitted is set as a target from which movement information is detected, the process described above may be performed by applying the CWD method. In this case, for the one-dimensional echo data generated through continuous wave transmission/reception, the PWD processing unit 14b serving as the CWD processing unit acquires one-dimensional blood flow information in time sequence of the scan line, and the image generator 15a generates a Doppler spectrum. Then, the Doppler spectrum generated by the CWD method is displayed together with the movement information data.

Figure 18:
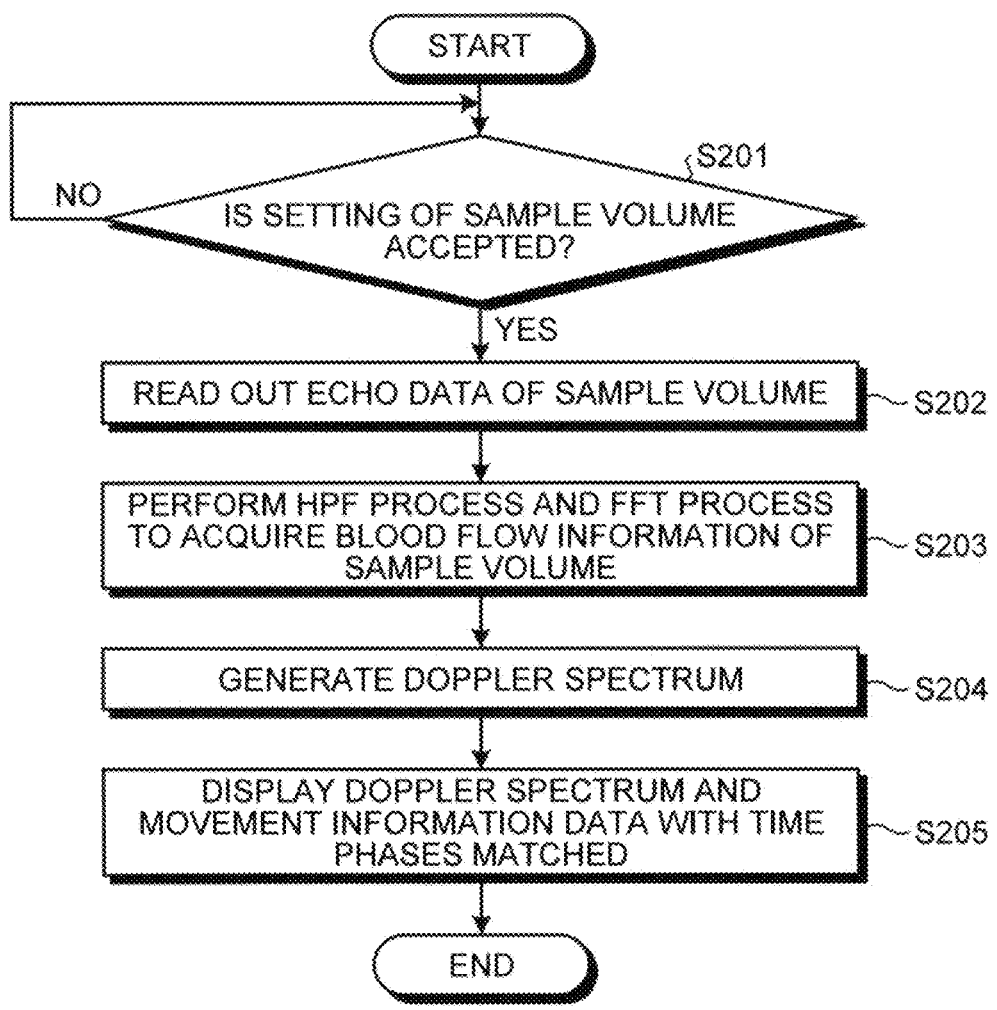
FIG. 18 is a flowchart for explaining processing in an ultrasonic diagnosis apparatus according to the second embodiment.

Next, using FIG. 18, the processing in the ultrasonic diagnosis apparatus according to the second embodiment will be described. FIG. 18 is a flowchart for explaining processing in the ultrasonic diagnosis apparatus according to the second embodiment. In the description of FIG. 18, after the movement information data is generated, scan for Doppler display is started, and concurrent display of a Doppler spectrum and movement information data is performed in real time concurrently with the scan for Doppler display.

As illustrated in FIG. 18, the controller 17 of the ultrasonic diagnosis apparatus according to the second embodiment determines whether the setting of a sample volume for Doppler display is accepted on a scan line included in the region of interest for movement information data display, from the operator (Step S201). Here, if the setting of a sample volume is not accepted (No at Step S201), the controller 17 waits until the setting of a sample volume is accepted.

On the other hand, if the setting of a sample volume is accepted (Yes at Step S201), the ultrasound probe 1 performs ultrasound transmission/reception on the scan line including the sample volume under the control of the transmitter/receiver 11, and the transmitter/receiver 11 generates echo data on the scan line from the echo signal received by the ultrasound probe 1 and stores the echo data into the frame buffer 12. Then, the PWD processing unit 14b reads out the echo data of the sample volume from the frame buffer 12 (Step S202) and performs the HPF process and the FFT process to acquire blood flow information of the sample volume (Step S203). The, the image generator 15a generates a Doppler spectrum (Step S204). Then, under the control of the controller 17, the monitor 2 displays the Doppler spectrum and the movement information data with the time phases matched (Step S205). The process then ends.

In the second embodiment, concurrent display of the Doppler spectrum and the movement information data may be performed after collection of the Doppler spectrum. In the second embodiment, the Doppler spectrum may be collected before collection of blood flow images. Also in the second embodiment, a plurality of ROIs for movement information data display may be set. In this case, scan for Doppler display is performed for each of a plurality of ROIs. Also in the second embodiment, the ROI for movement information data display may be three-dimensional.

As described above, in the second embodiment, Doppler display is performed together with movement information data display. In the PWD method, the aliasing velocity can be set higher than in the CFM method. Therefore, for blood flow with high flow rates, the FFT display by the PWD method is more reliable than by the CFM method. Then, as in the second embodiment, the Doppler spectrum according to the PWD method can be displayed concurrently with the blood flow image at high frame rate or the movement information data generated from the blood flow image, so that the operator can confirm the reliability of the blood flow image and the information concerning the blood flow behavior observed in the movement information data.

Figure 19:
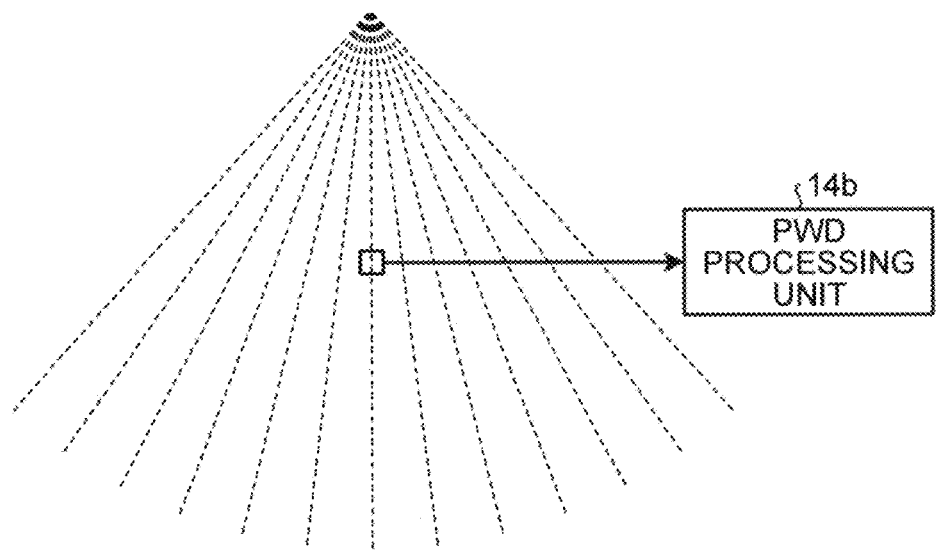
FIG. 19 and FIG. 20 are diagrams for explaining a third embodiment.
Figure 20:
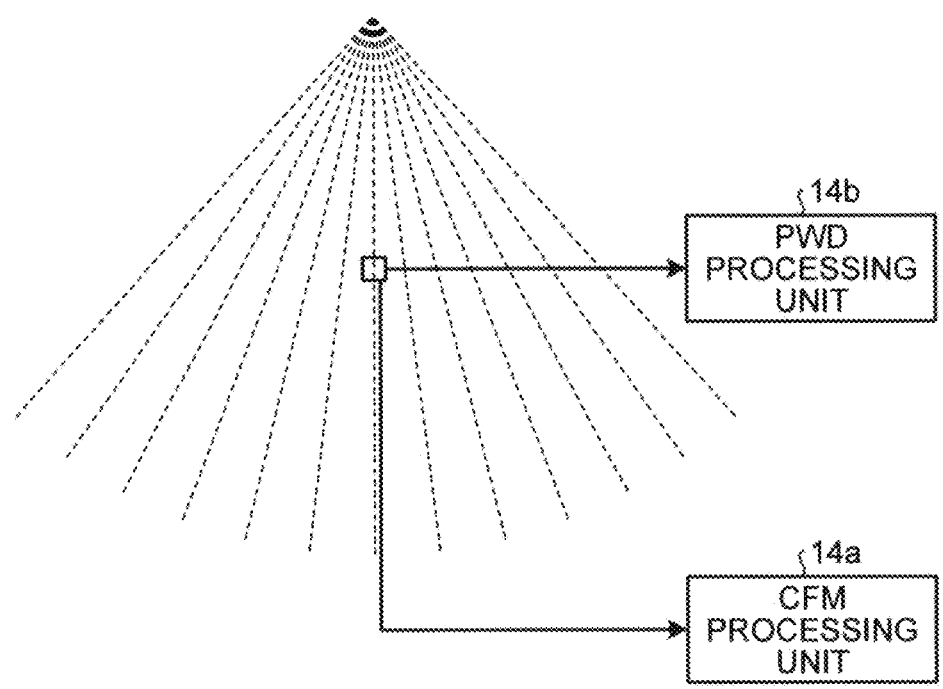

In a third embodiment, a case where movement information data is generated and displayed by fast fourier transform will be described using FIG. 19 and FIG. 20. FIG. 19 and FIG. 20 are diagrams for explaining the third embodiment.

In the second embodiment, the Doppler spectrum and the high frame rate blood flow image are separately collected, and the I/Q signal for generating the high frame rate blood flow image is retained, for example, in the frame buffer 12. Therefore, the PWD processing unit 14b can acquire the I/Q signal at any position in cross section of the high frame rate blood flow image.

Then, in the third embodiment, the PWD processing unit 14b acquires blood flow information in time sequence in a region of interest, for example, by performing frequency analysis by fast fourier transform, as explained using FIG. 13, on the echo data in the region of interest that is acquired from the frame buffer 12. More specifically, the PWD processing unit 14b acquires I/Q signals in time sequence in the ROI set at any position in the high frame rate blood flow image, as illustrated in FIG. 19, and performs the HPF process and the FFT process on the acquired I/Q signals in the frame direction. Accordingly, the PWD processing unit 14b can acquire blood flow information for generating a Doppler spectrum similar to the Doppler spectrum used in the conventional Doppler display. In other words, in the third embodiment, the ROI described in the first embodiment or the ROI set in that ROI is set as a sample volume.

The controller 17 controls the monitor 2 to display data in time sequence based on the blood flow information in time sequence in the region of interest. For example, in the third embodiment, the controller 17 can control to generate and display a Doppler spectrum, to generate and display a temporal change curve, or to generate and display a superimposed image, from the blood flow information in the ROI acquired through the FFT process.

Here, the PWD processing unit 14b can acquire, as the blood flow information, "velocity, distribution, and power" for each of a plurality of points set to generate the high frame rate blood flow image in the ROI. Alternatively, the PWD processing unit 14b can acquire, as average blood flow information, "average velocity, average distribution, and average power" in the ROI from "velocity, distribution, and power" for each of a plurality of points in the ROI. Alternatively, the PWD processing unit 14b can acquire average blood flow information at each of a plurality of ROIs by dividing an ROI into a plurality of ROIs.

Therefore, in the third embodiment, the controller 17 can allow the generation and displaying of a Doppler spectrum in an ROI, a Doppler spectrum for each of a plurality points in an ROI, or a Doppler spectrum for each of a plurality of ROIs set in an ROI, as a Doppler spectrum. In the third embodiment, the controller 17 can allow the generation and displaying of a temporal change curve in an ROI, a temporal change curve for each of a plurality of points in an ROI, or a temporal change curve for each of a plurality of ROIs set in an ROI, as a temporal change curve. In the third embodiment, the controller 17 can allow the generation and displaying of a superimposed image with an arrow showing average blood flow information in an ROI, a superimposed image with a plurality of arrows showing blood flow information at a plurality of points in an ROI, a superimposed image with an arrow showing blood flow information at a plurality of ROIs set in an ROI, or a superimposed image with a plurality of arrows showing blood flow information at a plurality of ROIs set in an ROI, as a superimposed image.

In the third embodiment, the PWD processing unit 14b, and the CFM processing unit 14a and the detector 15b may perform processing on the same echo data. More specifically, as illustrated in FIG. 20, the controller 17 may allow each of the CFM processing unit 14a and the PWD processing unit 14b to acquire blood flow information in an ROI. Given that output data of the CFM processing unit 14a is first blood flow information and output data of the PWD processing unit 14b is second blood flow information, the controller 17 controls to display a temporal change curve, a temporal change image, a superimposed image, etc. as movement information data based on the first blood flow information. Further, the controller 17 controls to display a Doppler spectrum, a temporal change curve, or a superimposed image as described above as movement information data based on the second blood flow information.

The ROI of the second blood flow information may be the same region as the ROI of the first blood flow information or may be set in the ROI of the first blood flow information. A plurality of ROIs of the second blood flow information may be set in the ROI of the first blood flow information. Also in the third embodiment, scan for FFT display may be additionally performed. Also in the third embodiment, if a region of interest including almost the entire scan line on which a continuous wave is transmitted is set as a target from which movement information is detected, the process described above may be performed by applying the CWD method.

Also in the third embodiment, when superimposed images are displayed in motion, a line marker showing the same time phase is displayed, for example, in a temporal change curve.

Next, using FIG. 21, the processing in the ultrasonic diagnosis apparatus according to the third embodiment will be described. FIG. 21 is a flowchart for explaining processing in the ultrasonic diagnosis apparatus according to the third embodiment. In FIG. 21, the ROI is set after collection of blood flow images, and the processing in the PWD processing unit 14b and the controller 17 as described above is performed after collection of blood flow images.

As illustrated in FIG. 21, the controller 17 of the ultrasonic diagnosis apparatus according to the third embodiment determines whether the setting of a region of interest is accepted as a sample volume from the operator (Step S301). Here, if the setting of a sample volume is not accepted (No at Step S301), the controller 17 waits until the setting of a sample volume is accepted.

On the other hand, if the setting of a sample volume is accepted (Yes at Step S301), the PWD processing unit 14b acquires echo data of the sample volume from the echo data retained for blood flow images (Step S302) and performs the HPF process and the FFT process to acquire blood flow information of the sample volume (Step S303). Then, the image generator 15a generates a Doppler spectrum (Step S304). Then, under the control of the controller 17, the monitor 2 displays a Doppler spectrum or a Doppler spectrum and movement information data with the time phases matched (Step S305). The process then ends. In the third embodiment, the ROI may be set before collection of echo data, and data such as a Doppler spectrum based on the blood flow information acquired through the FFT process from the echo data retained for blood flow images may be displayed in real time during capturing of blood flow images.

As described above, in the third embodiment, the blood blow behavior can be observed with more accurate position and time phase than in the second embodiment because the same signal as the high frame rate blood flow image is used for FFT display. However, in the third embodiment, PRF is inevitably low and the aliasing velocity is thus low when compared with the second embodiment in which echo data is separately collected, for example, by the PWD method. In other words, at a site where a flow rate is high as in the heart or carotid artery, for FFT display, the method described in the second embodiment has higher reliability in terms of the aliasing velocity. Therefore, the method in the third embodiment in which the same signal as in the high frame rate blood flow image is used for FFT display is preferably used in a case where a blood flow with relatively low velocity is observed. In the case where blood flow with relatively low velocity is to be observed, the method in the third embodiment is used to simplify the examination method and shorten the examination time because it is not necessary to separately perform scan for PWD.

The image processing described in the first embodiment to the third embodiment above may be executed by an image processing apparatus installed independent of a medical image diagnosis apparatus. Specifically, a database of the Picture Archiving and Communication System (PACS), which is a system for managing data of various medical images, or a database of an electronic chart system for managing electronic charts with medical images may store data retained in the frame buffer 12, and the image processing apparatus having the functions of the Doppler processing unit 14, the image processor 15, and the controller 17 may receive echo data from such a database and perform the image processing described above. When the image processing described in the first embodiment is performed, such an image processing apparatus may receive blood flow images generated at a frame rate of 60 fps or higher from the database and perform the image processing described above.

Each component of each apparatus illustrated in the drawing is a functionally conceptual component and may not be physically configured as illustrated. In other words, a specific manner of distribution and integration of the apparatus is not limited to the illustrated one, and the apparatus may be entirely or partially configured to be functionally or physically distributed or integrated in any unit depending on loads or use conditions. Furthermore, the processing functions performed in each apparatus may be entirely or partially implemented by a central processing unit (CPU) or a computer program analyzed and executed in the CPU, or as hardware formed of wired logic.

The image processing method described in the first embodiment to the third embodiment can be implemented by executing an image processing program prepared beforehand by a computer such as a personal computer or a workstation. The program can be distributed through a network such as the Internet. The image processing program can be stored in a computer-readable recording medium such as a hard disk, a flexible disk (FD), a compact disc read only memory (CD-ROM), an magnetooptical disc (MO), or a digital versatile disc (DVD), and may be read from the recording medium by a computer for execution.

As described above, according to the first embodiment to the third embodiment, the blood flow behavior in a two-dimensional or three-dimensional region of interest can be observed precisely with good time resolution.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnosis apparatus comprising:
a processor configured to collect a plurality of frames of two-dimensional or three-dimensional echo data in a manner of scanning in which ultrasound transmission/reception is performed in a plurality of scan lines that form a scan range of one frame, the ultrasound transmission/reception being performed once for each scan line in each frame, and acquire two-dimensional or three-dimensional blood flow information in time sequence in the scan range by comparing the plurality of frames of two-dimensional or three-dimensional echo data between frames;
an image generator configured to generate blood flow images in time sequence from the two-dimensional or three-dimensional blood flow information in time sequence in the scan range;
a detector configured to detect movement information in time sequence of speckles for each of a plurality of points in a preset two-dimensional or three-dimensional region of interest, among the blood flow images in time sequence; and
a controller configured to control the image generator to generate, based on the movement information in time sequence detected by the detector, movement information data in the form of a temporal change curve in which a representative value of the movement information in time sequence of speckles for each of the plurality of points is plotted in time sequence, or a temporal change image in which the temporal change curve is imaged, and to control a predetermined display to display the movement information data.

2. The ultrasonic diagnosis apparatus according to claim 1, wherein the processor is configured to acquire the two-dimensional or three-dimensional blood flow information in time sequence in the scan range by comparing the plurality of two-dimensional or three-dimensional echo data between frames using autocorrelation.

3. The ultrasonic diagnosis apparatus according to claim 1, wherein the controller is configured to control the image generator to generate, as the movement information data, a superimposed image in which predetermined graphics showing the movement information for each of the points are superimposed in the region of interest of the blood flow images.

4. The ultrasonic diagnosis apparatus according to claim 3, wherein the controller is configured to control the image generator to generate, as the movement information data, an image in which at least one of the representative value and a histogram showing distribution of values of the movement information at the points from which the representative value is calculated is superimposed at a predetermined position in the superimposed image.

5. The ultrasonic diagnosis apparatus according to claim 4, wherein when the superimposed image is to be displayed in motion concurrently with the temporal change curve or the temporal change image, the controller is configured to control to display a position corresponding to a time phase of the displayed superimposed image in the temporal change curve or the temporal change image.

6. The ultrasonic diagnosis apparatus according to claim 1, wherein
the processor is configured to perform frequency analysis on echo data collected through ultrasound transmission/reception separately performed on a scan line included in the region of interest to acquire blood flow information in time sequence on the scan line or blood flow information in time sequence in a sample volume on the scan line,
the image generator is configured to generate a Doppler spectrum in time sequence from the blood flow information in time sequence that is acquired through the frequency analysis, and
the controller is configured to control the predetermined display to display the Doppler spectrum and the movement information data in such a manner that the same time phase in both data is explicitly shown.

7. The ultrasonic diagnosis apparatus according to claim 6, wherein
the detector is configured to detect movement information in time sequence for each of a plurality of points in the region of interest, and
the controller is configured to control the image generator to generate, as the movement information data, a superimposed image in which predetermined graphics showing the movement information for each of the points are superimposed in the region of interest of the blood flow images, and, in a case where the superimposed image is displayed in motion concurrently with the Doppler spectrum, further control to display a position corresponding to a time phase of the displayed superimposed image in the Doppler spectrum.

8. The ultrasonic diagnosis apparatus according to claim 1, wherein a plurality of regions of interest are set.

9. The ultrasonic diagnosis apparatus according to claim 1, further comprising a memory configured to retain the plurality of frames of two-dimensional or three-dimensional echo data, wherein
the processor is configured to perform frequency analysis between frames on the plurality of frames of two-dimensional or three-dimensional echo data in the region of interest that is acquired from the memory to acquire blood flow information in time sequence in the region of interest, and
the controller is further configured to control the predetermined display to display, as the movement information data, data based on the blood flow information in time sequence in the region of interest that is acquired through the frequency analysis.

10. An ultrasonic diagnosis apparatus comprising:
a memory configured to retain a plurality of frames of two-dimensional or three-dimensional echo data collected in a manner of scanning in which ultrasound transmission/reception is performed in a plurality of scan lines that form a scan range in one frame, the ultrasound transmission/reception being performed once for each scan line in each frame;
a processor configured to acquire a plurality of frames of echo data in a preset two-dimensional or three-dimensional region of interest from the memory and to perform frequency analysis on the plurality of frames of acquired echo data between frames to acquire blood flow information in time sequence in the region of interest; and
a controller configured to control a predetermined display to display data in time sequence based on the blood flow information in time sequence in the region of interest.

11. An image processing apparatus comprising:
a detector configured to detect movement information in time sequence of speckles for each of a plurality of points in a preset two-dimensional or three-dimensional region of interest, among blood flow images in time sequence generated from two-dimensional or three-dimensional blood flow information in time sequence in a scan range by comparing a plurality of frames of two-dimensional or three-dimensional echo data between frames collected in a manner of scanning in which ultrasound transmission/reception is performed in a plurality of scan lines that form the scan range of one frame, the ultrasound transmission/reception being performed once for each scan line in each frame; and
a controller configured to control an image generator to generate, based on the movement information in time sequence detected by the detector, movement information data in the form of a temporal change curve in which a representative value of the movement information in time sequence of speckles for each of the plurality of points is plotted in time sequence, or a temporal change image in which the temporal change curve is imaged, and to control a predetermined display to display the movement information data.

12. An image processing method comprising:
detecting, by a detector, movement information in time sequence of speckles for each of a plurality of points in a preset two-dimensional or three-dimensional region of interest, among blood flow images in time sequence generated from two-dimensional or three- dimensional blood flow information in time sequence in a scan range by comparing a plurality of frames of two-dimensional or three-dimensional echo data between frames collected in a manner of scanning in which ultrasound transmission/reception is performed in a plurality of scan lines that form the scan range of one frame, the ultrasound transmission/reception being performed once for each scan line in each frame; and
controlling, by a controller, an image generator to generate, as the movement of information data that is data based on the movement information in time sequence, a temporal change curve in which a representative value of the movement information in time sequence of speckles for each of the plurality of points is plotted in time sequence, or a temporal change image in which the temporal change curve is imaged, and to control a predetermined display to display the movement information data.

* * * * *